United States Patent [19]

Martin

[11] Patent Number: 5,969,116
[45] Date of Patent: *Oct. 19, 1999

[54] NUCLEOSIDES AND OLIGONUCLEOTIDES HAVING 2'-ETHER GROUPS

[75] Inventor: Pierre Martin, Rheinfelden, Switzerland

[73] Assignee: Novartis Corporation, Summit, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/459,434

[22] Filed: Jun. 2, 1995

Related U.S. Application Data

[62] Division of application No. 08/241,213, May 10, 1994, abandoned.

[30] Foreign Application Priority Data

May 12, 1993 [CH] Switzerland .............................. 1467/9

[51] Int. Cl.⁶ ......................... C07H 19/00; A01N 43/04; C12Q 1/68
[52] U.S. Cl. ............................. 536/22.1; 435/6; 514/44; 536/23.1; 536/24.5
[58] Field of Search .................. 435/6; 514/44; 536/23.1, 24.5, 22.1

[56] References Cited

U.S. PATENT DOCUMENTS 5,212,295   5/1993   Cook ...................................... 536/26.7

FOREIGN PATENT DOCUMENTS

| | | |
|---|---|---|
| 266099 | 5/1988 | European Pat. Off. . |
| 8707300 | 12/1987 | WIPO . |
| 8908146 | 9/1989 | WIPO . |
| 9106556 | 5/1991 | WIPO . |
| WO91/10671 | 7/1991 | WIPO . |
| WO92/03568 | 3/1992 | WIPO . |
| WO93/13121 | 7/1993 | WIPO . |
| WO94/02501 | 2/1994 | WIPO . |

OTHER PUBLICATIONS

Beaucage, S.L. et al. Tetrahedron 48:2223–2311 (1992).
Cook, P.D., Anti–Cancer Drug Design 6:585–607 1991.
Englisch, U. et al. Angewandte Chemie 103:629–646 (1991).
Englisch, U. et al. Angewandte Chemie vol. 30, No. 6 (613–722) (1991) (International Edition).
C. Helene et al., Biochimica et Biophysica Acta, 1049(1990) 99–125.
Jenny, T. et al. Nucleosides & Nucleotides, 11(6), 1257–1261 (1992).
Marky, L.A. et al. Biopolymers 26:1601–1620 (1987).
Marques, V.E. et al. Medicinal Research Reviews 6:1–40 (1986).

(List continued on next page.)

*Primary Examiner*—Ardin H. Marschel
*Assistant Examiner*—Jezia Riley
*Attorney, Agent, or Firm*—Gregory D. Ferraro

[57] ABSTRACT

Compounds of the formula

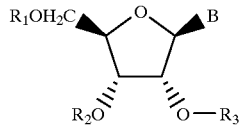

are described wherein $R_1$ and $R_2$ are each independently of the other hydrogen or a protecting group, or $R_1$ has those definitions and $R_2$ is a radical forming a phosphorus-containing nucleotide bridge group;

B is a purine or pyrimidine radical or an analogue thereof; and $R_3$ is a radical of formula Ia, Ib or Ic

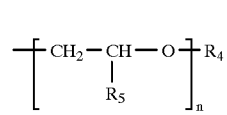 (Ia)

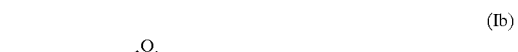

(Ib)

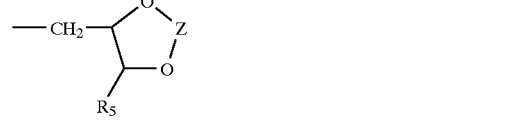

or

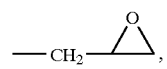 (Ic)

wherein $R_4$ is hydrogen, $C_1$–$C_{21}$alkyl, $C_2$–$C_{21}$alkenyl, $C_2$–$C_{21}$alkynyl or —C(=O)-alkyl;

$R_5$ is hydrogen, $C_1$–$C_{10}$alkyl, —$CH_2$—O—$R_6$ or a radical of formula Ib;

$R_6$ is hydrogen, $C_1$–$C_{22}$alkyl, $C_3$–$C_{21}$alkenyl, or partially or completely fluorine-substituted $C_1$–$C_{10}$alkyl or —[($CH_2$)$_2$—O]$_m$—$R_7$;

$R_7$ is hydrogen or $C_1$–$C_{21}$alkyl;

Z is —($CH_2$)$_p$— or —($CH_2$—$CH_2$—O)$_q$—$CH_2CH_2$—, it being possible for Z in the case of —$CH_2$— to be unsubstituted or substituted by one or more identical or different substituents selected from $C_1$–$C_{10}$alkyl, $C_5$–$C_6$cycloalkyl and unsubstituted or $C_1$–$C_4$alkyl-substituted phenyl;

n is a number from 1 to 12;

m is a number from 1 to 4;

p is a number from 1 to 10; and q is a number from 1 to 4.

16 Claims, No Drawings

OTHER PUBLICATIONS

Matteucci, M. et al. Annual Reports in Medicinal Chemistry 26:87–296 1991.

Sonveaux, E. Bioorganic Chemistry vol. 14, 274–325 (1986).

Uhlmann, E. et al. Chemical Review vol. 90, No. 4(1990) 543–584.

Iribarren et al., Proc. Natl. Acad. of Sci., 87:7747–7751 (1990).

Stein et al. "Antisense Oligonucleotides as Therapeutic Agents–Is the Bullet Really Magical?" Science, vol. 261, pp. 1004–1012, Aug. 1993.

Solomons "Organic Chemistry, Fifth Edition" John Wiley & Sons, Inc., pp. 431, 432, 699, 1992.

NUCLEOSIDES AND OLIGONUCLEOTIDES HAVING 2'-ETHER GROUPS

This application is a divisional of application Ser. No. 08/241,213 filed May 10, 1994, now abandoned.

The invention relates to ribo-nucleoside analogues, the 2'—OH group of which is etherified by polyol derivatives, to a process for the preparation thereof, to oligonucleotides having those nucleosides and to the use of the nucleosides in the preparation of oligonucleotides having identical or different nucleoside units in the molecule.

Nucleosides and oligonucleotides, both as antiviral active ingredients and because of their ability to interact with nucleic acids ("anti-sense" oligonucleotides), and the biological activity associated therewith, have attracted a great deal of interest; see, for example, Uhlmann, E., Peyman, A., Chemical Reviews 90:543–584 (1990). In order to produce nucleosides having new properties or to improve the interaction of anti-sense oligonucleotides with natural nucleic acids and to increase their stability towards nucleases, the sugar radicals of nucleosides (or of the nucleotide units of oligonucleotides) or the internucleotide phosphate bond in oligonucleotides have been modified in a wide variety of ways; see, for example, Marquez, V. E., Lim, M. I., Medicinal Research Reviews 6:1–40 (1986), Hélène, C., Toulmé, J. J., Biochimica et Biophysica Acta 1049:99–125 (1990), Englisch, U., Gauss, D. H., Angewandte Chemie 103:629–646 (1991), Matteucci, M. D., Bischofberger, N., Annual Reports in Medicinal Chemistry 26:87–296 (1991). Cook, P. D., Anti-Cancer Drug Design 6:585–607 (1991) and WO 91/106556 describe nucleosides that have been modified at the 2'—OH group of the sugar. The modifications described lead to increased nuclease resistance; the longer the alkyl radical, the higher the nuclease resistance. Thus with short alkyl radicals, such as methyl, ethyl or propyl, a slight increase in binding affinity is observed, while with relatively long chains the binding affinity falls dramatically. Nucleosides having polyol derivatives as side chains of the 2'—OH group are unknown and have never hitherto been incorporated into oligonucleotides. Surprisingly, the modifications according to the invention increase the binding affnity for complementary RNA not only in the case of relatively short chains but also in the case of relatively long chains. That result was not to be expected on the basis of the published data. Analogously to 2'—OH-modified oligoribonucleotides, the compounds of the invention are like-wise distinguished by their outstanding resistance to nuclease. In addition, oligonucleotides that comprise the nucleosides according to the invention have an increased cellular uptake and accordingly have greater bioavailability and activity in vivo.

The invention relates to compounds of formula I

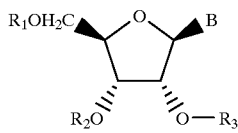

wherein $R_1$ and $R_2$ are each independently of the other hydrogen or a protecting group, or $R_1$ has those definitions and $R_2$ is a radical forming a phosphorus-containing nucleotide bridge group;

B is a purine or pyrimidine radical or an analogue thereof; and $R_3$ is a radical of formula Ia, Ib or Ic

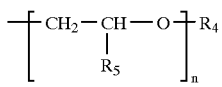

(Ia)

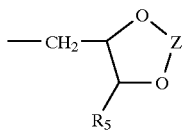

(Ib)

or

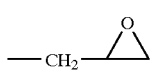

(Ic)

wherein $R_4$ is hydrogen, $C_1$–$C_{21}$alkyl, $C_2$–$C_{21}$alkenyl, $C_2$–$C_{21}$alkynyl or —C(=O)-alkyl;

$R_5$ is hydrogen, $C_1$–$C_{10}$alkyl, —CH$_2$—O—$R_6$ or a radical of formula Ib;

$R_6$ is hydrogen, $C_1$–$C_{22}$alkyl, $C_3$–$C_{21}$alkenyl, or partially or completely fluorine-substituted $C_1$–$C_{10}$alkyl or —[(CH$_2$)$_2$—O]$_m$—$R_7$;

$R_7$ is hydrogen or $C_1$–$C_{21}$alkyl;

Z is —(CH$_2$)$_p$— or —(CH$_2$—CH$_2$—O)$_q$—CH$_2$CH$_2$—, it being possible for Z in the case of —CH$_2$— to be unsubstituted or substituted by one or more identical or different substituents selected from $C_1$–$C_{10}$alkyl, $C_5$–$C_6$cycloalkyl and unsubstituted or $C_1$–$C_4$alkyl-substituted phenyl;

n is a number from 1 to 12;

m is a number from 1 to 4;

p is a number from 1 to 10; and q is a number from 1 to 4;

and $R_4$ is not hydrogen when n=1 and $R_5$=hydrogen.

In a preferred form, $R_4$ is hydrogen, $C_1$–$C_{21}$alkyl, $C_2$–$C_{21}$alkenyl or $C_2$–$C_{21}$alkynyl. In a more preferred form, $R_4$ is hydrogen, $C_1$–$C_8$alkyl, $C_2$–$C_8$alkenyl or $C_2$–$C_8$alkynyl. In an especially preferred form, $R_4$ is hydrogen or $C_1$–$C_4$alkyl. Examples of $R_4$ are methyl, ethyl, n- and iso-propyl, n-, iso- and tert-butyl, and the isomers of pentyl, hexyl, heptyl, octyl, nonyl, decyl, undecyl, dodecyl, tridecyl, tetradecyl, pentadecyl, hexadecyl, heptadecyl, octadecyl, nonadecyl, undecyl, vinyl, allyl, but-3-en-1-yl, but-2-en-1-yl, pentenyl, octenyl, dodecenyl, octadecenyl, ethynyl, prop-1-yn-1-yl, prop-1-yn-3-yl, but-1-yn-1-yl or but-1-yn-4-yl. Radicals $R_4$ that are especially preferred are hydrogen, methyl, ethyl, n- or iso-propyl or n-butyl. The value of n is preferably from 1 to 8, more preferably from 1 to 6 and especially from 1 to 3.

In a preferred form, $R_5$ is hydrogen, $C_1$–$C_5$alkyl or —CH$_2$—O—$R_6$, especially hydrogen, methyl or —CH$_2$—OH, —CH$_2$—O—$C_1$–$C_{22}$alkyl or —CH$_2$—O—[(CH$_2$)$_2$—O]$_m$—$C_1$–$C_{10}$alkyl, wherein m is a number from 1 to 4.

In a preferred form, $R_1$ and $R_2$ are hydrogen.

Protecting groups and processes for derivatising hydroxy groups having such protecting groups are generally known in sugar and nucleotide chemistry and are described, for example, by Greene, B. T., Protective Groups in Organic Synthesis, Wiley Interscience, New York (1991), by Sonveaux, E., Bioorganic Chemistry 14:274–325 (1986) or by Beaucage, S. L., Iyer, R., Tetrahedron 48:2223–2311 (1992). Examples of such protecting groups are: benzyl, methylbenzyl, dimethylbenzyl, methoxybenzyl, dimethoxybenzyl, bromobenzyl, 2,4dichlorobenzyl; diphenylmethyl, di(methylphenyl)methyl, di(dimethylphenyl)methyl, di(methoxyphenyl)methyl, di(dimethoxyphenyl)methyl, triphenylmethyl, tris-4,4',4"-tert-butylphenylmethyl, di-p-anisylphenylmethyl, tri(methylphenyl)methyl, tri(dimethylphenyl)methyl, methoxyphenyl(diphenyl)methyl, di(methoxyphenyl)phenylmethyl, tri(methoxyphenyl)methyl, tri(dimethoxyphenyl)methyl; triphenylsilyl, alkyldiphenylsilyl, dialkylphenylsilyl and trialkylsilyl having from 1 to 20, preferably from 1 to 12, and especially from 1 to 8, carbon atoms in the alkyl groups, for example trimethylsilyl, triethylsilyl, tri-n-propylsilyl, isopropyl-dimethylsilyl, tert-butyl-dimethylsilyl, tertbutyl-diphenylsilyl, n-octyl-dimethylsilyl, (1,1,2,2-tetramethylethyl)-dimethylsilyl, —($C_1$–$C_8$alkyl)$_2$Si—O—Si($C_1$–$C_8$alkyl)$_2$—, wherein alkyl is, for example, methyl, ethyl, n- and viso-propyl or n-, iso- or tert-butyl; $C_2$–$C_{12}$acyl, especially $C_2$–$C_8$acyl, such as acetyl, propanoyl, butanoyl, pentanoyl, hexanoyl, benzoyl, methylbenzoyl, methoxybenzoyl, chlorobenzoyl and bromobenzoyl; $R_{S1}$—SO$_2$— wherein $R_{S1}$ is $C_1$–$C_{12}$alkyl, especially $C_1$–$C_6$alkyl, $C_5$- or $C_6$-cycloalkyl, phenyl, benzyl, $C_1$–$C_{12}$alkylphenyl, especially $C_1$–$C_4$alkylphenyl, or $C_1$–$C_{12}$alkylbenzyl, especially $C_1$–$C_4$alkylbenzyl, or halophenyl or halobenzyl, for example methyl-, ethyl-, propyl-, butyl-, phenyl-, benzyl-, p-bromo-, p-methoxy- and p-methylphenyl-sulfonyl; $C_1$–$C_{12}$alkoxycarbonyl, preferably $C_1$–$C_8$alkoxycarbonyl, that is unsubstituted or substituted by F, Cl, Br, $C_1$–$C_4$alkoxy, tri($C_1$–$C_4$alkyl)silyl or by $C_1$–$C_4$alkylsulfonyl, for example methoxy-, ethoxy-, n- or iso-propoxy- or n-, iso- or tert-butoxycarbonyl, 2-trimethylsilylethoxycarbonyl, 2-methylsulfonylethoxycarbonyl, allyloxycarbonyl, or phenoxycarbonyl or benzyloxycarbonyl that is unsubstituted or is substituted as for alkoxycarbonyl, for example methyl- or methoxy- or chlorophenoxycarbonyl or methyl- or methoxy- or chlorobenzyloxycarbonyl, and 9-fluorenylmethoxycarbonyl. If $R_1$ and/or $R_2$ are(is) alkyl, they may be substituted by fluorine, chlorine, bromine, $C_1$–$C_4$alkoxy, phenoxy, chlorophenoxy, methoxyphenoxy, benzyloxy, methoxybenzyloxy or by chlorophenoxy. $R_1$ and $R_2$ in formula I may be identical or different protecting groups.

In an especially preferred form, $R_1$ and $R_2$, as protecting groups, may be benzyl, methylbenzyl, dimethylbenzyl, methoxybenzyl, dimethoxybenzyl, halogenated benzyl, especially bromobenzyl; diphenylmethyl, di(methylphenyl)methyl, di(dimethylphenyl)methyl, di(methoxyphenyl)methyl, di(methoxyphenyl)(phenyl)methyl, triphenylmethyl, tris-4,4',4"-tert-butylphenylmethyl, di-p-anisylphenylmethyl, tri(methylphenyl)methyl, tri(dimethylphenyl)methyl, tri(methoxyphenyl)methyl, tri(dimethoxyphenyl)methyl; trimethylsilyl, triethylsilyl, tri-n-propylsilyl, isopropyl-dimethylsilyl, tert-butyldimethylsilyl, tert-butyldiphenylsilyl, n-octyldimethylsilyl, (1,1,2,2-tetramethylethyl)-dimethylsilyl, —(CH$_3$)$_2$Si—O—Si(CH$_3$)$_2$—, —(iso—C$_3$H$_7$)$_2$Si—O—Si(iso—C$_3$H$_7$)$_2$—; acetyl, propanoyl pentanoyl, hexanoyl, benzoyl, methylbenzoyl, methoxybenzoyl, chlorobenzoyl and bromobenzoyl; methyl-, ethyl-, propyl-, butyl-, phenyl-, benzyl-, p-bromo-, p-methoxy- and p-methyl-phenylsulfonyl; methoxy-, ethoxy-, n- or iso-propoxy- or n-, iso- or tert-butoxycarbonyl, or phenoxycarbonyl, benzyloxycarbonyl, methyl- or methoxy- or chloro-phenoxycarbonyl or methyl- or methoxy- or chloro-benzyloxycarbonyl or 9-fluorenylmethoxycarbonyl. In this case, $R_1$ and $R_2$ are advantageously identical protecting groups.

$R_2$ as a phosphorus-containing, nucleotide-bridge-group-forming radical may correspond to formula P1 or P2

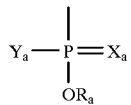

(P1)

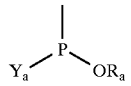

(P2)

wherein $Y_a$ is hydrogen, $C_1$–$C_{12}$alkyl, $C_6$–$C_{12}$aryl, $C_7$–$C_{20}$aralkyl, $C_7$–$C_{20}$alkaryl, —OR$_b$, —SR$_b$, —NH$_2$, primary amino, secondary amino, O$^\ominus$M$^\oplus$ or S$^\ominus$M$^\oplus$;

$X_a$ is oxygen or sulfur;

$R_a$ is hydrogen, M$^\oplus$, $C_1$–$C_{12}$alkyl, $C_2$–$C_{12}$alkenyl or $C_6$–$C_{12}$aryl, or the group $R_aO$— is N-heteroaryl-N-yl having 5 ring members and from 1 to 3 nitrogen atoms;

$R_b$ is hydrogen, $C_1$–$C_{12}$alkyl or $C_6$–$C_{12}$aryl; and

M$^\oplus$ is Na$^\oplus$, K$^\oplus$, Li$^\oplus$, NH$_4^\oplus$ or primary, secondary, tertiary or quaternary ammonium;

alkyl, aryl, aralkyl and alkaryl in $Y_a$, $R_a$ and $R_b$ being unsubstituted or substituted by alkoxy, alkylthio, halogen, —CN, —NO$_2$, phenyl, nitrophenyl or halophenyl.

$Y_a$ contains as primary amino preferably from 1 to 12 and especially from 1 to 6 carbon atoms, and as secondary amino preferably from 2 to 12 and especially from 2 to 6 carbon atoms.

The primary amino and the secondary amino may be, for example, radicals of the formula $R_cR_dN$, wherein $R_c$ is hydrogen or, independently, has the meaning of $R_d$, and $R_d$ is $C_1$–$C_{20}$-, preferably $C_1$–$C_{12}$- and especially $C_1$–$C_6$-alkyl, $C_1$–$C_{20}$-, preferably $C_1$–$C_{12}$- and especially $C_1$–$C_6$-aminoalkyl or $C_1$–$C_{20}$-, preferably $C_1$–$C_{12}$- and especially $C_1$–$C_6$-hydroxyalkyl; carboxyalkyl or carbalkoxyalkyl, the carbalkoxy group containing from 2 to 8 carbon atoms and the alkyl group from 1 to 6, preferably from 1 to 4, carbon atoms; $C_2$–$C_{20}$-, preferably $C_2$–$C_{12}$- and especially $C_2$–$C_6$-alkenyl; phenyl, mono- or di-($C_1$–$C_4$alkyl or $C_1$–$C_4$alkoxy) phenyl, benzyl, mono- or di-($C_1$–$C_4$alkyl or $C_1$–$C_4$alkoxy) benzyl; or 1,2-, 1,3- or 1,4-imidazolyl-$C_1$–$C_6$alkyl, or $R_c$ and $R_d$ together are tetra- or penta-methylene, 3-oxa-1,5-pentylene, —CH$_2$—NR$_e$—CH$_2$CH$_2$— or —CH$_2$CH$_2$—NR$_{19}$—CH$_2$CH$_2$—, wherein $R_e$ is hydrogen or $C_1$–$C_4$alkyl. The amino group in aminoalkyl may be substituted by one or two $C_1$–$C_4$alkyl or $C_1$–$C_4$hydroxyalkyl groups. The hydroxy group in hydroxyalkyl may be etherified by $C_1$–$C_4$alkyl.

Primary, secondary, tertiary and quaternary ammonium for $Y_a$ in connection with the definition of M$^\oplus$ is to be understood as being an ion of the formula $R_fR_gR_hR_iN^\oplus$, wherein $R_f$ is $C_1$–$C_{20}$-, preferably $C_1$–$C_{12}$- and especially $C_1$–$C_6$-alkyl, $C_1$–$C_{20}$-, preferably $C_1$–$C_{12}$- and especially $C_1$–$C_6$-aminoalkyl, $C_1$–$C_{20}$-, preferably $C_1$–$C_{12}$- and especially $C_1$–$C_6$-hydroxyalkyl; carboxyalkyl or carbalkoxyalkyl, the carbalkoxy group containing from 2 to 8 carbon atoms and the alkyl group from 1 to 6, preferably from 1 to 4, carbon atoms; $C_2-C_{20}$-, preferably $C_2-C_{12}$- and especially $C_2-C_6$-alkenyl; phenyl, mono- or di-($C_1-C_4$alkyl or $C_1-C_4$alkoxy)phenyl, benzyl, mono- or di-($C_1-C_4$alkyl or $C_1-C_4$alkoxy)benzyl; or 1,2-, 1,3- or 1,4-imidazolyl-$C_1-C_6$alkyl, and $R_g$, $R_h$ and $R_i$ are each independently of the others hydrogen or have the definition of $R_f$, or $R_f$ and $R_g$ together are tetra- or pentamethylene, 3-oxa-1,5-pentylene, —CH$_2$—NR$_e$—CH$_2$CH$_2$— or —CH$_2$CH$_2$13 NR$_e$—CH$_2$CH$_2$—, wherein $R_e$ is hydrogen or $C_1-C_4$alkyl, and $R_h$ and $R_i$ each independently of the other have the definition of $R_f$. The amino group in aminoalkyl may be substituted by one or two $C_1-C_4$alkyl or $C_1-C_4$hydroxyalkyl groups. The hydroxy group in the hydroxyalkyl may be etherified by $C_1-C_4$alkyl.

Examples of carboxyalkyl are carboxymethyl, carboxyethyl, carboxypropyl and carboxybutyl, and examples of carbalkoxyalkyl are those carboxyalkyl groups esterified by methyl or ethyl. Examples of alkenyl are allyl, but-1-en-3-yl or 4-yl, pent-3- or -4-en-1-yl or -2-yl, hex-3- or -4- or -5-en-1-yl or -2-yl. Examples of alkyl- and alkoxyphenyl and alkyl-and alkoxy-benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl and diethoxybenzyl. Examples of imidazolylalkyl in which the alkyl group preferably contains from 2 to 4 carbon atoms are 1,2-, 1,3- or 1,4-imidazolyl-ethyl or -n-propyl or -n-butyl. $R_{19}$ is preferably hydrogen, methyl or ethyl.

Preferred examples of primary amino and secondary amino are methyl-, ethyl-, dimethyl-, diethyl-, diisopropyl, mono- or di-(1-hydroxy-eth-2-yl)-, phenyl- and benzyl-amino, acetylamino and benzoylamino and piperidinyl, piperazinyl and morpholinyl.

Preferred examples of primary and secondary ammonium are methyl-, ethyl-, dimethyl-, diethyl-, diisopropyl-, mono- or di-(1-hydroxy-eth-2-yl)-, phenyl- and benzyl-ammonium.

Examples of $Y_a$, $R_a$ and $R_b$ as alkyl are methyl, ethyl and the isomers of propyl, butyl, pentyl, hexyl, heptyl and octyl; examples of $Y_a$, $R_a$ and $R_b$ as aryl are phenyl and naphthyl; examples of $R_a$ as alkenyl are allyl and ($C_1-C_4$alkyl)CH=CH—CH$_2$—; examples of $Y_a$ as aralkyl are phenyl-$C_nH_{2n}$— wherein n is a number from 1 to 6, especially benzyl; examples of $Y_a$ as alkaryl are mono-, di- and tri-($C_1-C_4$alkyl)phenyl. Preferred substituents are chlorine, bromine, methoxy, —NO$_2$, —CN, 2,4-dichlorophenyl and 4-nitrophenyl. Examples of $R_b$ are 2,2,2-trichloroethyl, 4-chlorophenyl, 2-chlorophenyl and 2,4-dichlorophenyl; and examples of $R_bO$— as N-heteroaryl are pyrrol-N-yl, triazol-N-yl and benzotriazol-N-yl.

In an especially preferred form, $R_a$ is β-cyanoethyl and $Y_a$ is di(isopropylamino).

If B is a purine radical or an analogue thereof, it may be a radical of formula II, IIa, IIb, IIc, IId, IIe or IIf

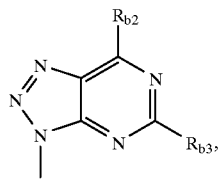
(II)

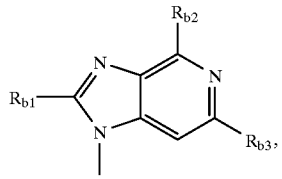
(IIa)

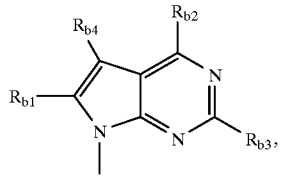
(IIb)

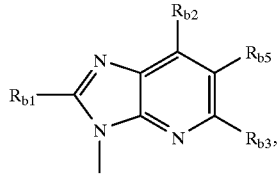
(IIc)

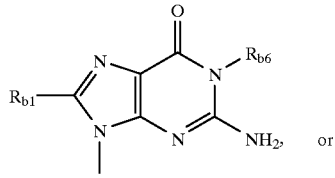
(IId)

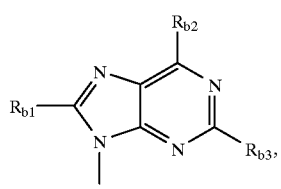
(IIe)

or

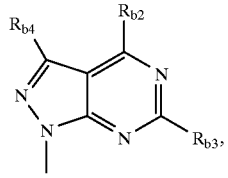
(IIf)

wherein
$R_{b1}$ is H, Cl, Br, OH or —O—$C_1-C_{12}$alkyl, and
$R_{b2}$, $R_{b3}$ and $R_{b5}$ are each independently of the others H, OH, SH, NH$_2$, NHNH$_2$, NHOH, NHO—$C_1-C_{12}$alkyl, —N=CH—N($C_1-C_{12}$alkyl)$_2$, —N=CH—N-cycloalkyl, F, Cl, Br, $C_1-C_{12}$alkyl, hydroxy-$C_1-C_{12}$alkyl, amino-$C_1-C_{12}$alkyl, $C_1-C_{12}$alkoxy, benzyloxy or $C_1-C_{12}$-alkylthio, the hydroxy and amino groups being unsubstituted or substituted by a protecting group; or phenyl, benzyl, primary amino having from 1 to 20 carbon atoms or secondary amino having from 2 to 30 carbon atoms,
$R_{b4}$ is hydrogen, CN or —C≡C—$R_{b7}$, and
$R_{b6}$ and $R_{b7}$ are hydrogen or $C_1-C_4$alkyl.

Suitable protecting groups are mentioned hereinbefore. Preferred protecting groups are $C_1$–$C_8$acyl groups, such as acetyl, propionyl, butyroyl and benzoyl. $R_{b6}$ is preferably hydrogen or methyl.

The primary amino contains preferably from 1 to 12, and especially from 1 to 6, carbon atoms, and the secondary amino contains preferably from 2 to 12, and especially from 2 to 6, carbon atoms.

Some examples of alkyl, alkoxy, alkylthio, hydroxyalkyl and aminoalkyl containing preferably from 1 to 6 carbon atoms are methyl, ethyl and the isomers of propyl, butyl, pentyl, hexyl, heptyl, octyl, nonyl, decyl, undecyl and dodecyl, and corresponding alkoxy, alkylthio, hydroxyalkyl and aminoalkyl radicals. Alkyl, alkoxy, alkylthio, hydroxyalkyl and aminoalkyl contain especially from 1 to 4 carbon atoms. Preferred alkyl, alkoxy, alkylthio, hydroxyalkyl and aminoalkyl radicals are methyl, ethyl, n- and iso-propyl, n-, iso- and tert-butyl, methoxy, ethoxy, methylthio and ethylthio, aminomethyl, aminoethyl, hydroxymethyl and hydroxyethyl.

The primary amino and the secondary amino may be, for example, radicals of the formula $R_{a1}R_{a2}N$, wherein $R_{a1}$ is hydrogen or, independently, has the definition of $R_{a2}$, and $R_{a2}$ is $C_1$–$C_{20}$-, preferably $C_1$–$C_{12}$- and especially $C_1$–$C_6$-alkyl, $C_1$–$C_{20}$-, preferably $C_1$–$C_{12}$- and especially $C_1$–$C_6$-aminoalkyl, $C_1$–$C_{20}$-, preferably $C_1$–$C_{12}$- and especially $C_1$–$C_6$-hydroxyalkyl; carboxyalkyl or carbalkoxyalkyl, the carbalkoxy group containing from 2 to 8 carbon atoms and the alkyl group from 1 to 6, preferably from 1 to 4, carbon atoms; $C_2$–$C_{20}$-, preferably $C_2$–$C_{12}$- and especially $C_2$–$C_6$-alkenyl; phenyl, mono- or di-($C_1$–$C_4$alkyl or $C_1$–$C_4$alkoxy) phenyl, benzyl, mono- or di-($C_1$–$C_4$alkyl or $C_1$–$C_4$alkoxy) benzyl; or 1,2-, 1,3- or 1,4-imidazolyl-$C_1$–$C_6$alkyl, or $R_{a1}$ and $R_{a2}$ together are tetra- or penta-methylene, 3-oxa-1,5-pentylene, —$CH_2$—$NR_{a3}$—$CH_2CH_2$— or —$CH_2CH_2$—$NR_{a3}$—$CH_2CH_2$—, wherein $R_{a3}$ is hydrogen or $C_1$–$C_4$alkyl. The amino group in aminoalkyl may be substituted by one or two $C_1$–$C_4$alkyl or $C_1$–$C_4$hydroxyalkyl groups. The hydroxy group in hydroxyalkyl may be etherified by $C_1$–$C_4$alkyl.

Examples of alkyl are given hereinbefore. Examples of aminoalkyl are aminomethyl, aminoethyl, 1-aminoprop-2-yl or -3-yl, 1-amino-but-2-yl or -3-yl or -4-yl, N-methyl- or N,N-dimethyl- or N-ethyl- or N,N-diethyl- or N-2-hydroxyethyl- or N,N-di-2-hydroxyethyl-aminomethyl or -aminoethyl or -aminopropyl or -aminobutyl. Examples of hydroxyalkyl are hydroxymethyl, 1-hydroxy-eth-2-yl, 1-hydroxy-prop-2- or -3-yl and 1-hydroxy-but-2-yl, -3-yl or -4-yl. Examples of carboxyalkyl are carboxymethyl, carboxyethyl, carboxypropyl and carboxybutyl, and examples of carbalkoxyalkyl are those carboxyalkyl groups esterifed by methyl or by ethyl. Examples of alkenyl are allyl, but-1-en-3-yl or -4-yl, pent-3- or -4-en-1-yl or -2-yl, hex-3- or -4- or -5-en-1-yl or -2-yl. Example of alkyl- and alkoxy-phenyl and alkyl- and alkoxy-benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl and diethoxybenzyl. Examples of imidazolylalkyl in which the alkyl group preferably contains from 2 to 4 carbon atoms are 1,2-, 1,3- or 1,4-imidazolyl-ethyl or -n-propyl or -n-butyl. $R_{a3}$ is preferably hydrogen, methyl or ethyl.

Preferred examples of primary amino and secondary amino are methyl-, ethyl-, dimethyl-, diethyl-, allyl-, mono- or di-(1-hydroxy-eth-2-yl)-, phenyl- and benzyl-amino, acetyl-amino, isobutyrylamino and benzoylamino.

In a preferred form, $R_{b1}$ is hydrogen. In another preferred form, $R_{b5}$ is hydrogen. In a further preferred form, $R_{b2}$ and $R_{b3}$ are each independently of the other H, F, Cl, Br, OH, SH, $NH_2$, NHOH, $NHNH_2$, methylamino, dimethylamino, benzoylamino, isobutyryl-amino, methoxy, ethoxy and methylthio.

Some examples of analogues of the purine series are, in addition to purine, xanthine, hypoxanthine, adenine, N-methyladenine, N-benzoyladenine, 2-methylthioadenine, 2-aminoadenine, 6-hydroxypurine, 2-amino-6-chloropurine, 2-amino-6-methylthiopurine, guanine, N-isobutyrylguanine. Especially preferred are adenine, 2-aminoadenine and guanine, and the base-protected derivatives thereof.

If B in formula I is a pyrimidine radical, it is preferably a uracil, thymine or cytosine radical of formula III, IIIa, IIIb or IIIc

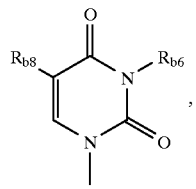

(III)

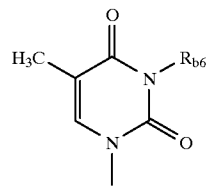

(IIIa)

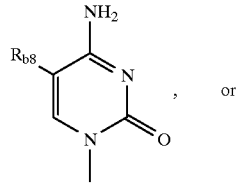

(IIIb)

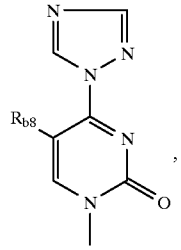

(IIIc)

wherein $R_{b6}$ is hydrogen or $C_1$–$C_4$alkyl and $R_{b8}$ is H, OH, SH, $NH_2$, $NHNH_2$, NHOH, NHO—$C_1$–$C_{12}$alkyl, —N=CH—N($C_1$–$C_{12}$alkyl)$_2$, —N=CH—N-cycloalkyl, F, Cl, Br, $C_1$–$C_{12}$alkyl, hydroxy-$C_1$–$C_{12}$alkyl, amino-$C_1$–$C_{12}$alkyl, $C_1$–$C_{12}$alkoxy, benzyloxy or $C_1$–$C_{12}$alkylthio, the hydroxy and amino groups being unsubstituted or substituted by a protecting group, or is phenyl, benzyl, primary amino having from 1 to 20 carbon atoms, secondary amino having from 2 to 30 carbon atoms, $C_1$–$C_{12}$alkenyl or $C_1$–$C_{12}$alkynyl, and the $NH_2$ group in formula IIIb is unsubstituted or substituted by $C_1$–$C_6$alkyl, benzoyl or by a protecting group, and the dihydro derivatives of the radicals of formulae III, IIIa, IIIb and IIIc. $R_{b8}$ in formula III is preferably hydrogen, $C_1$–$C_6$alkyl or $C_1$–$C_6$hydroxyalkyl, $C_2$–$C_6$alkenyl or $C_2$–$C_6$alkynyl, F, Cl, Br, $NH_2$, benzoylamino or mono- or di-$C_1$–$C_6$alkylamino. $R_{b8}$ in formulae IIIb and IIIc is preferably hydrogen, $C_1$–$C_6$alkyl or $C_1$–$C_6$alkoxy or $C_1$–$C_6$hydroxyalkyl, $C_2$–$C_6$alkenyl or $C_2$–$C_6$alkynyl, F, Cl, Br, $NH_2$, benzoylamino or mono- or di-$C_1$–$C_6$alkylamino.

$R_{b6}$ is preferably hydrogen or methyl. $R_{b8}$ in formula III is preferably H, F, Cl, Br, $NH_2$, $NHCH_3$, $N(CH_3)_2$, $C_1$–$C_4$alkyl, $C_2$–$C_4$alkenyl or $C_2$–$C_4$alkyn-1-yl. $R_{b8}$ in formula IIIb and IIIc is preferably hydrogen, $C_1$–$C_4$alkyl, especially methyl, $C_2$–$C_4$alkenyl, especially vinyl, or $C_2$–$C_4$alkyn-1-yl, especially 1-propyn-1-yl, or $NH_2$, $NHCH_3$ or $(CH_3)_2N$.

Some examples of pyrimidine analogues are uracil, thymine, cytosine, 5-fluorouracil, 5-chlorouracil, 5-bromouracil, dihydrouracil, 5-methylcytosine, 5-propynethymine and 5-propynecytosine.

The invention relates also to a process for the preparation of compounds of formula I

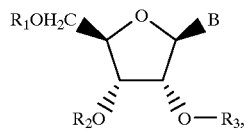

(I)

wherein $R_1$ and $R_2$ are each independently of the other hydrogen or a protecting group or $R_1$ has those definitions and $R_2$ is a radical forming a phosphorus-containing nucleotide bridge group; B is a purine or pyrmidine radical or an analogue thereof; and (a) $R_3$ is a radical of formula Ia

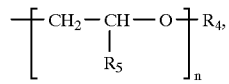

(Ia)

wherein
$R_4$ is hydrogen, $C_1$–$C_{21}$alkyl, $C_2$–$C_{21}$alkenyl, $C_2$–$C_{21}$alkynyl or —C(=O)alkyl;
$R_5$ is hydrogen, $C_1$–$C_{10}$alkyl, —$CH_2$—O—$R_6$ or a radical of formula Ib;
$R_6$ is hydrogen, $C_1$–$C_{22}$alkyl, $C_3$–$C_{21}$alkenyl, partially or completely fluorine-substituted $C_1$–$C_{10}$alkyl or —[$(CH_2)_2$—O]$_m$—$R_7$;
$R_7$ is hydrogen or $C_1$–$C_{21}$alkyl;
n is a number from 1 to 12; and
m is a number from 1 to 4;
and R4 is not hydrogen when n=1 and $R_5$=hydrogen,
which process comprises
reacting a compound of formula IVa

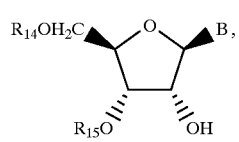

(IVa)

wherein $R_{14}$ and $R_{15}$ are identical or different protecting groups and B is a purine or pyrimidine radical or an analogue thereof, functional groups in the base radical B being protected by protecting groups, in an inert solvent, with a compound of formula A

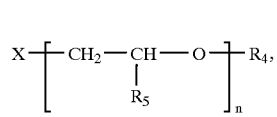

(A)

wherein $R_4$, $R_5$ and n are as defined above nd X is Cl, Br, I, tosyl-O or mesyl-O;

(b) $R_3$ is a radical of formula Ic

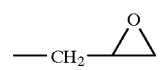

(Ic)

which process comprises reacting a compound of formula IVa in an inert solvent with a compound of formula B

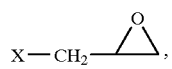

(B)

wherein X is Cl, Br, I, tosyl-O or mesyl-O;

(c) $R_3$ is a radical of formula Ib

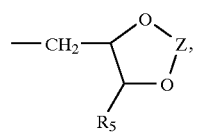

(Ib)

wherein
$R_5$ is hydrogen, $C_1$–$C_{10}$alkyl, —$CH_2$—O—$R_6$ or a radical of formula Ib;
$R_6$ is hydrogen, $C_1$–$C_{22}$alkyl, $C_3$–$C_{21}$alkenyl, partially or completely fluorine-substituted $C_1$–$C_{10}$alkyl or —[$(CH_2)_2$—O]$_m$—$R_7$;
$R_7$ is hydrogen or $C_1$–$C_{21}$alkyl;
Z is —$(CH_2)_p$— or —$(CH_2$—CH—O)$_q$—$CH_2CH_2$—, it being possible for Z in the case of —$CH_2$— to be unsubstituted or substituted by one or more identical or different substituents selected from $C_1$–$C_{10}$alkyl, $C_5$–$C_6$cycloalkyl and unsubstituted or $C_1$–$C_4$alkyl-substituted phenyl;
m is a number from 1 to 4;
p is a number from 1 to 10; and
q is a number from 1 to 4;
which process comprises opening the epoxide obtained in (b) in the presence of $H_2O$ and $BF_3$ and closing it with a compound of formula X'—$(CH_2)_q$—X' or X'—$(CH_2$—CH—O)$_r$—X', wherein X' is Cl, Br, I, tosyl-O or mesyl-O, to form a new ring;

(d) $R_3$ is a radical of formula Ia, which process comprises reacting the epoxide obtained in (b) in the presence of $R_6OH$ and $BF_3$ and, where appropriate, converting the freed hydroxy group into an ether or an ester, (e) $R_3$ is a radical of formula Ia, which process comprises hydrogenating the epoxide obtained in (b) in the presence of $BF_3$ and, for example, $NaBH_4$, and, where appropriate, converting the freed hydroxy group into an ether or an ester, (f) $R_3$ is a radical of formula Ia, which process comprises reacting the epoxide obtained in (b) with a suitable Grignard reagent and, where appropriate, converting the freed hydroxy group into an ether or an ester; or g) $R_3$ is a radical of formula Ia, Ib or Ic, which process comprises substituting at the 2'—OH group by one of the processes described in (a) to (f) a compound of formula IVb

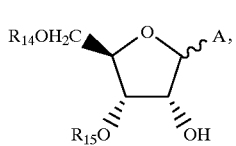

(IVb)

wherein $R_{14}$ and $R_{15}$ are as defined above and A is a leaving group, preferably alkoxy, acyloxy, mesyl-O, tosyl-O and especially $OCH_3$, $OCOCH_3$ and benzoyloxy, and then, in a manner known per se, introducing the base radical B by substitution [(Lukevics, E., Zablocka, A., Nucleoside Synthesis, Ellis Horwood, New York (1991)], where appropriate removing the protecting groups $R_{14}$ and $R_{15}$, and introducing the radical forming the phosphorus-containing nucleotide bridge group.

Compounds of formula I wherein $R_5$ is hydrogen and n=1 are also obtained by reacting a compound of formula IVa with a compound of formula X—$CH_2$—CO—OR, subsequently reducing the CO group to a $CH_2OH$ group and then alkylating the latter.

The compounds of formulae IVa and IVb, A and B are known; some of them are commercially available or can be prepared by known or analogous methods.

Inert solvents are, for example, hydrocarbons, halogenated hydrocarbons, alkylated carboxylic acid amides and lactams, ethers, nitriles, such as acetonitrile, dialkylsulfones or dialkylsulfoxides or cyclic sulfones and sulfoxides.

The reaction temperatures in process steps (a) to (g) are from $-50$ to $200°$ C., preferably from 0 to $90°$ C.

The reactions are advantageously carried out in the presence of bases, for example alkali metal hydrides, alcoholates, hydroxides, carbonates, trialkylamines or diazabicycloundecene.

The reaction may be carried out, for example, catalytically or with borohydrides.

The compounds of formula I are isolated and purified by methods known per se, such as precipitation or crystallisation and filtration and chromatographic methods.

The compounds of formula I can be used to build oligonucleotides which, owing to their interaction with nucleic acids, exhibit valuable biological activity, and can be used as pharmaceutical active ingredients or as diagnostic agents.

The invention relates also to the use of the compounds of formula I in the preparation of oligonucleotides comprising identical or different monomer units of compounds of formula I, but at least one monomer unit of compounds of formula I in combination with monomer units of other natural or synthetic nucleosides, the oligonucleotides comprising from 2 to 200 monomer units. The oligonucleotides comprise preferably from 2 to 100, especially from 2 to 50, and most especially from 4 to 30, monomer units. Preference is given to oligonucleotides comprising identical or different monomer units of compounds of formula I. Preference is also given to oligonucleotides additionally comprising monomer units of synthetic or natural nucleosides derived from D-ribose or D-deoxy-ribose.

The invention relates also to oligonucleotides of formula V

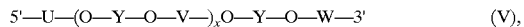

wherein x is a number from 0 to 200 and Y is a nucleotide bridge group, U, V and W are, each individually, identical or different radicals of natural or synthetic nucleosides, and at least one of the radicals U, V and/or W is a radical of formula VI

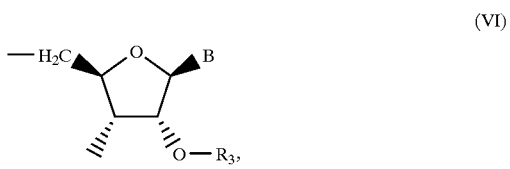

(VI)

and B and $R_3$ are as defined for compounds of formula I, including the preferences and examples.

A preferred bridge group Y is the group —P(O)O$^\ominus$— which occurs in natural oligonucleotides. Examples of further bridge groups are —P(O)S$^\ominus$—, —P(S)S$^\ominus$—, —P(O)$R_{16}$—, P(O)N—$R_{17}R_{18}$, and —$CH_2$—, wherein $R_{16}$ is hydrogen or $C_1$-$C_6$alkyl and $R_{17}$ and $R_{18}$ each independently of the other have the definition of $R_{16}$. In formula V, x is preferably a number from 0 to 100, especially a number from 1 to 50, and more especially a number from 3 to 29. The radicals of formula VI may be bonded terminally or in the nucleotide sequence, it being possible for all or several, for example from 2 to 5, radicals of formula VI to follow one another, or the radicals of formula VI may be bonded between radicals of natural or synthetic nucleosides, or mixed forms of those distributions may be present in the nucleotide sequence.

An especially preferred form are oligonucleotides of formula V wherein x is a number from 2 to 50, preferably from 2 to 30, Y is the group —P(O)O$^\ominus$—, U, V and W are, each individually, identical or different radicals of a natural nucleoside and at least one of the radicals U, V or W corresponds to formula VI. Suitable natural nucleosides are adenosine, cytidine, guanosine, uridine, 2-aminoadenine, 5-methylcytosine, 2'-deoxyadenosine, 2'-deoxycytidine, 2'-deoxyguanosine and thymidine. There may be mentioned as natural nucleoside bases especially adenine, cytosine, guanine, thymine and uracil. The radicals of formula VI may be bonded terminally or in the nucleotide sequence, it being possible for all or several, for example from 2 to 5, identical or different radicals of formula VI to follow one another, or identical or different radicals of formula VI being bonded between radicals of natural nucleosides, or mixed forms of those distributions being present in the nucleotide sequence. In another preferred form of oligonucleotides of formula V, all the radicals U, V and W are identical or different radicals of formula VI. x is preferably a number from 3 to 29 and the total number of radicals of formula VI is preferably from 1 to 12.

The oligonucleotides according to the invention can be prepared in a manner known per se by various methods in optionally automated DNA synthesisers that are commercially available together with processing instructions. In the case of the bridge group —P(O)O$_\ominus$— there may be used, for example, the phosphorus triester method, the phosphite triester method or the H-phosphonate method, which are familiar to a person skilled in the art. The phosphite triester method can be carried out, for example, as follows: the nucleosides of formula I wherein $R_1$ and $R_2$ are each hydrogen are reacted with a protecting group reagent, for example 4,4'-dimethoxytriphenylmethyl chloride, to form a nucleoside of formula D

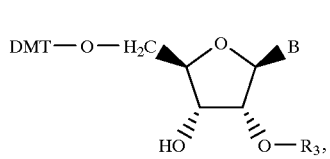

(D)

and the compound of formula D is bound with the aid of a "linker", for example succinic acid anhydride, to a solid carrier, for example to controlled pore glass (CPG), containing long-chained alkylamino groups. In a separate process, the hydroxy group of the compound of formula D is derivatised, for example to a phosphorus amidite, using R'OP[N(isopropyl)$_2$)]$_2$ to form a compound of formula E

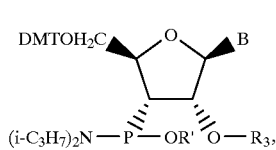

(E)

wherein R' is, for example, β-cyanoethyl.

When the protecting group, such as the DMT group of the material bound to the carrier, has been removed, coupling is effected, with removal of —N(iso-C$_3$H$_7$)$_2$, to the compound of formula D, any free hydroxy groups are blocked (capping) and the phosphite that has formed is then oxidised to the phosphate. The dimer is deprotected and the reaction cycle is then repeated with a compound of formula E until an oligomer having the desired number of monomer units has been synthesised, and the product is removed from the carrier. In that way, oligonucleotides are obtained in which all the radicals U, V and W according to formula V consist of radicals of formula VI. The same method can be used to prepare oligonucleotides having any desired monomer units in any desired sequence, the units and their sequence depending on which synthetic and natural nucleoside building blocks and nucleoside building blocks according to the invention are used in the individual reaction cycles.

The compounds of formula I according to the invention wherein $R_1$ and $R_2$ are each hydrogen have antiviral and antiproliferative properties and can accordingly be used as medicaments. The oligonucleotides according to the invention have, in addition, a high degree of stability towards degradation by nucleases. Especially surprising is their excellent pairing with complementary nucleic acid strands, especially of the RNA type. In addition, they exhibit an unexpectedly high cellular uptake. The oligonucleotides according to the invention are therefore suitable especially for anti-sense technology, that is to say, for inhibiting the expression of undesired protein products by binding to suitable complementary nucleotide sequences of mRNA (EP 266 099, WO 87/07300 and WO 89/08146). They can be used in the treatment of infections and diseases, for example by blocking the expression of bioactive proteins at the nucleic acid (for example oncogene) stage. The oligonucleotides of the invention are suitable also as diagnostic agents and can be used as gene probes in the detection of viral infections or genetic diseases by selective interaction at the single- or double-stranded nucleic acid stage. In particular, owing to their increased stability towards nucleases, they can be used diagnostically not only in vitro but also in vivo (for example tissue samples, blood plasma and blood serum). Such possible uses are described, for example, in WO 91/06556.

The invention relates further to the use of the oligonucleotides according to the invention as diagnostic agents in the detection of viral infections or genetic diseases.

The invention relates also to the use of the nucleosides of formula I according to the invention and of the oligonucleotides of formula V in a therapeutic method for the treatment of diseases in warm-blooded animals including humans by inactivating nucleotide sequences in the body. The dosage in the case of administration to warm-blooded animals having a body weight of approximately 70 kg may be, for example, from 0.01 to 1000 mg per day. Administration, preferably in the form of pharmaceutical compositions, is effected parenterally, for example intravenously or intraperitoneally.

The invention relates further to a pharmaceutical composition comprising an effective amount of a nucleoside of formula I or of an oligonucleotide of formula V alone or together with other active ingredients, a pharmaceutical carrier, preferably in a significant amount, and, where appropriate, excipients.

The pharmacologically active nucleosides and oligonucleotides according to the invention can be used in the form of parenterally administrable compositions or infusion solutions. Such solutions are preferably isotonic aqueous solutions or suspensions, it being possible, for example in the case of lyophilised compositions comprising the active ingredient alone or together with a carrier, for example mannitol, for those solutions or suspensions to be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions, which may, if desired, comprise further pharmacologically active substances, such as antibiotics, are prepared in a manner known per se, for example by means of conventional dissolving or lyophilising methods, and comprise approximately from 0.1% to 90%, especially from approximately 0.5% to approximately 30%, for example from 1% to 5%, active ingredient(s).

The Examples that follow illustrate the invention. The $^1$H-NMR-spectra are based on the numbering of the carbon atoms in the following cyclic carbon structures:

Starting compounds:

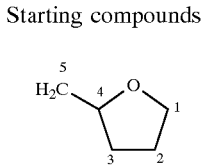

Nucleosides (examples):

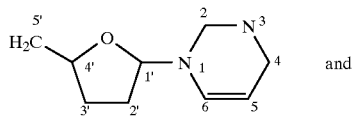 and

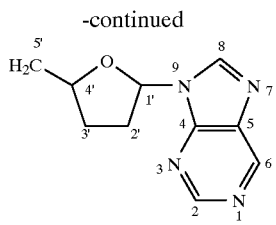

Abbreviations used in the text and in the formulae:

| | |
|---|---|
| DMF | dimethylformamide |
| ClBnCl$_2$ | 2,4-dichlorobenzyl chloride |
| Bn | benzyl |
| Ac | acetyl |
| φ | phenyl |
| BSA | N,N-bistrimethylsilylacetamide |
| DBU | diazabicyclo[5.4.0.]undec-7-ene |
| BOM—CL | benzyloxymethyl chloride |
| DMTCl | 4,4'-dimethoxytrityl chloride |
| THF | tetrahydrofuran |

A) Preparation of Nucleoside Analogues

EXAMPLE A1

28.0 g of 1-methylribose are added dropwise to 13.5 g of NaH in 130 ml of DMF at 60° C. When the evolution of H$_2$ has ceased, 110.0 g of ClBnCl$_2$ are added drop-wise. The reaction mixture is then stirred for 16 hours at 25° C. In order to destroy any remaining NaH, methanol is carefully added dropwise thereto and the reaction mixture is then poured onto ice/water. The lumpy precipitate is filtered off and then washed thoroughly with acetonitrile to yield the compound (A1).

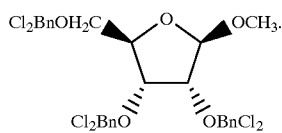
(A1)

$^1$H-NMR (250 MHz, CDCl$_3$): the H—C(1)-proton appears at 5.0 ppm as a singlet. MS: 638 (M$^+$)

EXAMPLE A2

65.9 g of the product prepared in Example A1 are dissolved in 600 ml of methylene chloride and cooled to 0° C. 121 ml of SnCl$_4$ in 800 ml of methylene chloride are then added dropwise thereto and the reaction mixture is left to stand at 3° C. After 26 hours a further 2 ml of SnCl$_4$ are added. After a total of 35 hours the reaction solution is poured carefully onto 700 ml of a saturated NaHCO$_3$ solution. After dilution with 400 ml of methylene chloride the Sn-containing precipitate is filtered off. The organic phase of the filtrate is dried with MgSO$_4$ and concentrated by evaporation to yield the compound (A2).

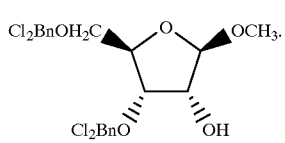
(A2)

$^1$H-NMR (250 MHz, CDCl$_3$): the H—C(1)-proton appears at 4.90 ppm as a doublet with J=5 Hz.

EXAMPLE A3

125.9 g of the product obtained in Example A2 are dissolved in 1 liter of pyridine. At 20° C., 25.5 g of acetic anhydride and 1 g of 4-dimethylaminopyridine are added. The reaction mixture is then stirred for 17 hours, is taken up in 1 liter of water, acidified with concentrated hydrochloric acid and extracted with ethyl acetate. The extract is dried with MgSO$_4$ and concentrated by evaporation. Finally, the residue is crystallised with hexane to yield the compound (A3).

(A3)

$^1$H-NMR (250 MHz, CDCl$_3$): 5.15 [d, J=4.5 Hz, H—C(1)]; 3.50 (s, OCH$_3$); 2.17 (s, OCOCH$_3$); MS: 522 (M$^+$) [α]$_{Na(D)}$=87.4±1.0°, CHCl$_3$ (0.998%)

EXAMPLE A4

24 g of thymine are made into a slurry in 100 ml of 1,2-dichloroethane. After the addition of 116.4 g of BSA, the reaction mixture is heated under reflux until a clear solution forms. The reaction mixture is then cooled to 50° C. and 50 g of the product prepared in Example A3 and 27.5 g of trifluoromethanesulfonic acid trimethylsilyl ester are added thereto. The reaction mixture is stirred for 20 hours at 70° C. and then poured onto 300 ml of NaHCO$_3$ solution and stirred. After extraction with dichloroethane, the reaction mixture is dried with MgSO$_4$ and concentrated by evaporation. Finally, the residue is crystallised with methanol to yield the compound (A4).

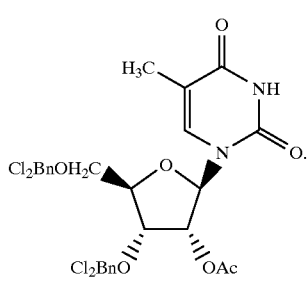
(A4)

$^1$H-NMR (250 MHz, CDCl$_3$): 8.25 (s, NH); 6.10 [d, J=4.5 Hz, H—C(1')]; 2.13 (s, OCOCH$_3$); 1.66 (s,CH$_3$) MS: 616 (M$^+$)

EXAMPLE A5

85 g of the product prepared in Example A4 are suspended in 850 ml of acetonitrile. At room temperature, 24.2 g of DBU and 24.9 g of BOM-Cl are added drop-wise thereto. The reaction mixture is stirred for 20 hours and then poured onto water and extracted with ethyl acetate. The extract is dried with MgSO₄ and concentrated by evaporation ation to yield the compound (A5).

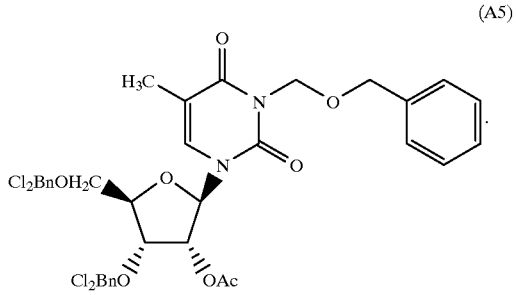

(A5)

$^1$H-NMR (250 MHz, CDCl$_3$): 6.05 [d, J=4.5 Hz, H—C(1')]; 5.5 (AB, CH$_2$); 5.37 [dd, H—C(2')]; 2.13 (s, OCOCH$_3$); 1.55 (s, CH$_3$) MS: 736 (M$^+$)

EXAMPLE A6

106 g of the product prepared in Example A5 are suspended in 1 liter of THF and 26 g of a 30% NaOCH$_3$/CH$_3$OH solution are added dropwise thereto. After stirring for 2.5 hours, the reaction solution is poured onto water, saturated aqueous sodium chloride solution is added thereto and the reaction solution is extracted with ethyl acetate. After drying with MgSO$_4$, the extract is concentrated by evaporation to yield the compound (A6).

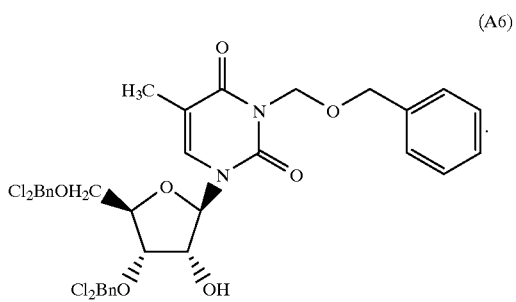

(A6)

$^1$H-NMR (250 MHz, CDCl$_3$): 5.93 [d, J=5 Hz, H—C(1')]; 5.5 (AB, CH$_2$); 3.03 (d, J=6.5 Hz, OH); 1.72 (s, CH$_3$) MS: 694 (M$^+$)

EXAMPLE A7

20.3 g of the product obtained in Example A6 are dissolved in 200 ml of THF. 0.73 g of NaH are added thereto and the reaction mixture is boiled for 30 min. Then 2.89 g of 2-chloroethyl methyl ether are added and the reaction mixture is boiled for a further 24 hours. A further 0.5 g of NaH and 1.7 g of 2-chloroethyl methyl ether are then added and boiling is continued. After a total of 32 hours, the reaction mixture is poured onto water and extracted with ethyl acetate. The extract is dried with MgSO$_4$ and concentrated by evaporation. The residue is chromatographed on silica gel with toluene/ethyl acetate (4:1) to yield the compound (A7).

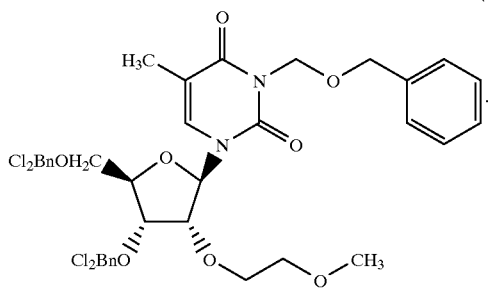

(A7)

$^1$H-NMR (250 MHz, CDCl$_3$): 7.65 [s, H—C(6)]; 5.93 [s, H—C(1')]; 5.5 (s, CH$_2$); 3.33 (s, OCH$_3$); 1.6 (s, CH$_3$). MS: 752 (M$^+$).

EXAMPLE A8

79.4 g of the product obtained in Example A6 are dissolved in 800 ml of THF. 3.3 g of NaH are added and the reaction mixture is brought to the boil for a short time and then, at 40° C., 21 g of bromoacetic acid methyl ester are added dropwise thereto. The reaction mixture is stirred for a total of 27 hours at 60° C., 1 g of NaH and 2 ml of bromoacetic acid methyl ester being added after 16 hours and after 20 hours. Finally, the reaction mixture is poured onto water and extracted with ethyl acetate. The extract is dried with MgSO$_4$ and concentrated by evaporation to yield the compound (A8).

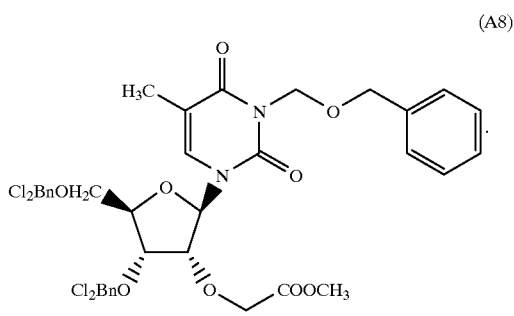

(A8)

$^1$H-NMR (250 MHz, CDCl$_3$): 7.70 [s, H—C(6)]; 5.92 [s, H—C(1')]; 5.48 (AB, CH$_2$); 3.75 (s, OCH$_3$); 1.58 (s, CH$_3$). MS: 766 (M$^+$).

EXAMPLE A9 a) 37 g of the product obtained in accordance with Example A8 are dissolved in 400 ml of THF. At 20° C., 1.5 g of LiBH$_4$ are added in portions thereto and the reaction mixture is stirred for 1 hour. The reaction mixture is then poured carefully onto 500 ml of water and neutralised with 32 ml of 2 N aqueous hydrochloric acid. Extraction with ethyl acetate and concentration by evaporation yield the compound (A9).

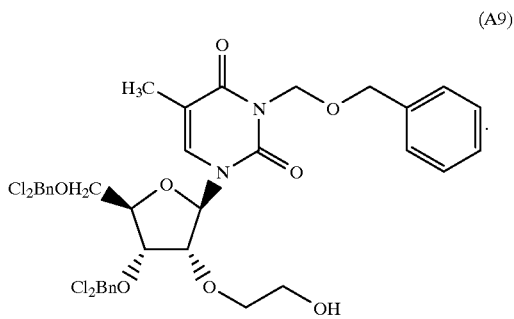

(A9)

¹H-NMR (250 MHz, CDCl₃): 7.65 [s, H—C(6)]; 5.96 [s, H—C(1')]; 5.50 (AB, CH₂); 2.57 (broad s, OH); 1.60 (s, CH₃). MS: 738 (M⁺).

b) The compound (A9) is methylated with CH₃I in the presence of NaH in THF at 70° C. After 8 hours, working up is effected as described in Example A7 to yield the compound (A7).

EXAMPLE A10

20.0 g of the product prepared in Example A7 are dissolved in 200 ml of THF and hydrogenated for 4.5 hours over 2 g of Pd/C (5%) at 25° C. and under normal pressure (H₂-uptake 102%). After filtration and concentration of the filtrate by evaporation, the residue is dissolved in 170 ml of methanol and the pH is adjusted to 11 with a 30% NaOCH₃/CH₃OH solution. After 24 hours, the reaction mixture is poured onto 250 ml of water, acidified with 2 N aqueous hydrochloric acid and extracted with ethyl acetate. The extract is dried with MgSO₄ and concentrated by evaporation to yield the compound (A10).

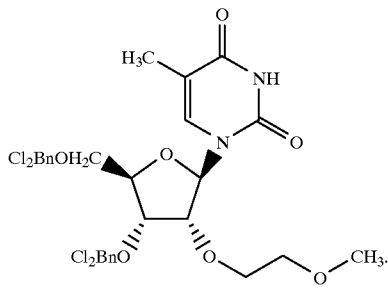

(A10)

¹H-NMR (250 MHz, CDCl₃): 8.75 (s, NH); 7.65 [s, H—C(6)]; 5.97 [s, H—C(1')]; 3.33 (s, OCH₃); 1.60 (s, CH₃). MS: 632 (M⁺).

EXAMPLE A11

15 g of the product prepared in Example A10 are hydrogenated in 250 ml of methanol in the presence of 9.25 g of anhydrous sodium acetate over 5 g of Pd/C (5%) at 50° C. and under normal pressure. After 46 hours, the hydrogenation mixture is filtered and concentrated by evaporation. To remove salts, the residue is chromatographed over a small frit with silica gel (ethyl acetate/methanol 9:1). The compound (A11) is obtained.

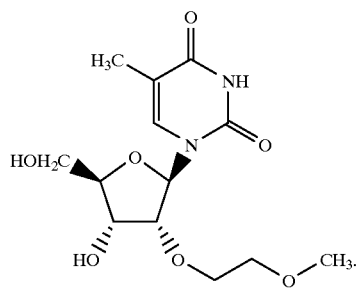

(A11)

¹H-NMR (250 MHz, CDCl₃): 11.5 (s, NH); 7.95 [s, H—C(6)]; 6.00 [d, J=6 Hz, H—C(1')]; 5.33 (broad s, OH); 5.20 (d, OH); 3.32 (s, OCH₃); 1.92 (s, CH₃). MS: 316 (M⁺).

EXAMPLE A12

0.45 g of the product prepared in Example A11 is twice taken up in pyridine and concentrated by evaporation. It is again taken up in 18 ml of pyridine and there are then added in succession: 0.2 g of triethylamine, 0.55 g of DMTCl and 25 mg of 4dimethylaminopyridine. The reaction mixture is stirred for 16 hours at room temperature and then diluted with 50 ml of ethyl acetate and poured onto 50 ml of water. The organic phase is dried with MgSO₄ and concentrated. The residue is chromatographed over silica gel (hexane/ethyl acetate/triethylamine 86:10:4) to yield the compound (A12).

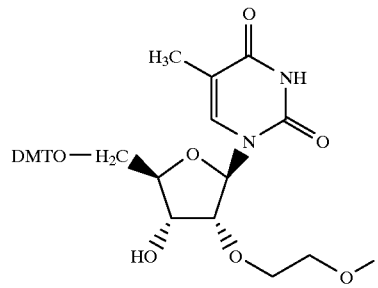

(A12)

1H-NMR (250 MHz, CDCl₃): 7.62 [s, H—C(6)]; 6.02 [d, J=4 Hz, H—C(1')]; 3.38 (s, OCH₃); 1.36 (s, CH₃).

EXAMPLE A13

330 mg of the product obtained in Example A12 are added to 110 mg of diisopropylammonium tetrazolide, 178 mg of 2-cyanoethyl-N,N,N',N'-tetraisopropylphosphorus diamidite and 6 ml of methylene chloride. The reaction mixture is stirred for 17 hours at room temperature and then poured onto a saturated aqueous NaHCO₃ solution. The organic phase is dried with MgSO₄ and concentrated by evaporation. The residue is chromatographed over silica gel (ethanol/ethyl acetate 4:1 with 1% addition of triethylamine). The resulting foam is dissolved in 1 ml of methyl tert-butyl ether and added drop-wise at 0° C. to pentane to yield the compound (A13) (diastereoisomers, 1:1).

(A13)

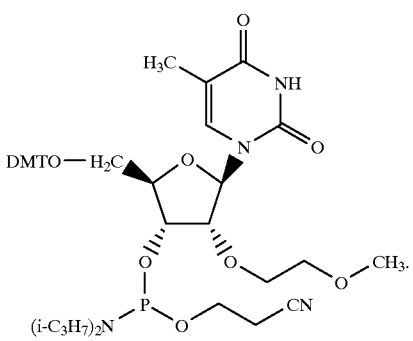

$^1$H-NMR (250 MHz, CDCl$_3$): 7.70 [s, H—C(6)] and 7.63 [s, H—C(6)]; 6.08 [d, J=4 Hz, H—C(1')]; 6.02 [d, J=4 Hz, H—C(1')].

EXAMPLE 14

24.2 g of the product obtained in Example A2 are dissolved in 250 ml of THF. 8.76 g of bromoacetic acid methyl ester and 1.38 g of NaH are added thereto and the reaction mixture is then stirred for 3.5 hours at 60° C. After the addition of a further 0.14 g of NaH and a further 0.53 ml of bromoacetic acid methyl ester, the reaction mixture is stirred for a further 3 hours at 60° C. The suspension is then poured onto 300 ml of water, neutralised with 2 N aqueous hydrochloric acid and extracted with ethyl acetate. The extract is dried over MgSO$_4$ and concentrated by evaporation to yield the compound (A14).

(A14)

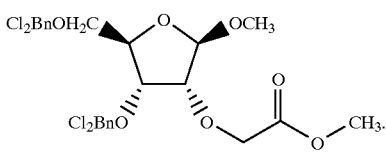

$^1$H-NMR (250 MHz, CDCl$_3$): 5.05 [d, J=4 Hz, H—C(1')]; 3.50 [s, OCH$_3$] and 3.75 [s, OCH$_3$]. MS: 552 (M$^+$).

EXAMPLE A15

5.0 g of the product obtained in Example A14 are dissolved in 60 ml of acetonitrile. 4.88 g of bisilylated thymine are then added and, with stirring at 60° C., 2.6 g of trifluoromethanesulfonic acid trimethylsilyl ester are added dropwise thereto. After stirring for 3.5 hours, the reaction solution is cooled, poured onto a saturated aqueous NaHCO$_3$ solution and stirred. The reaction solution is then extracted with ethyl acetate and the organic phase is dried with MgSO$_4$ and concentrated by evaporation. The residue is chromatographed over silica gel (toluene/ethyl acetate 1:1) to yield the compound A15).

(A15)

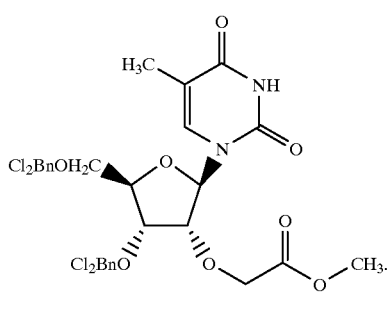

$^1$H-NMR (250 MHz, CDCl$_3$): 8.36 (s, NH); 7.70 [s, H—C(6)]; 5.94 [d, J=1.5 Hz, H—C(1')]; 3.73 (s, OCH$_3$); 1.58 [s, CH$_3$]. MS: 646 (M$^+$).

b) Reaction with benzyloxymethyl chloride yields the compound (A8).

EXAMPLE A16

Further 2'—OH modifications are carried out analogously to the above instructions, and these are listed in Table 1.

TABLE 1

Examples of further 2'-OH modifications (a)

| B | R$_3$ | H—C(1') |
|---|---|---|
| U$^{BOM}$ | CH$_3$CH$_2$OCH$_3$ | 5.93(s) |
| U$^{BOM}$ | (CH$_2$CH$_2$O)$_3$CH$_3$ | 5.93(s) |
| U$^{BOM}$ | CH$_2$COOCH$_3$ | 5.89(d, J<1.5Hz) |
| T$^{BOM}$ | (CH$_2$CH$_2$O)$_2$CH$_3$ | 5.97(s) |
| T$^{BOM}$ | (CH$_2$CH$_2$O)$_4$CH$_3$ | 5.96(s) |
| T$^{BOM}$ | CH$_2$CH$_2$OH | 5.96(s) |
| T$^{BOM}$ | CH$_2$CH$_2$OAc | 5.98(d, J=2Hz) |
| T$^{BOM}$ | CH$_2$COOCH$_3$ | 5.92(s) |
| T$^{BOM}$ | CH$_2$CH$_2$OCH$_3$ | 5.93(s) |
| T$^{BOM}$ | (CH$_2$CH$_2$O)$_3$CH$_3$ | 5.96(d, J=2Hz) |

TABLE 1-continued

Examples of further 2'-OH modifications

| Base | 2'-OH modification | Chemical shift |
|---|---|---|
| $T^{BOM}$ | $CH_2CH(OH)CH_3$ | 5.92(s) |
| $T^{BOM}$ | $CH_2CH(OH)CH_2OH$ | 5.94(brs) |
| $T^{BOM}$ | $CH_2CH(OCH_3)CH_3$ | 5.97(s) |
| $T^{BOM}$ | $(CH_2CH_2O)_3C_{10}H_{21}$ | 5.93(d, J=1.5Hz) |
| $T^{BOM}$ | $CH_2CH(OH)CH_2OC_{16}H_{33}$ | 5.93(s) |
| $T^{BOM}$ | $CH_2CH(OCH_3)CH_2OC_{16}H_{33}$ | 5.97(d, 1.5Hz) |
| $T^{BOM}$ | $CH_2CH(OAc)CH_2O(CH_2CH_2O)_3CH_3$ | 5.93(s) |
| $T^{BOM}$ | $CH_2CH(OH)CH_2O(CH_2CH_2O)_3CH_3$ | 5.98(d, J=1.5Hz) |
| $T^{BOM}$ | $CH_2$-(epoxide) (R) | 5.91(s) |
| $T^{BOM}$ | $CH_2$-(2,2-dimethyl-1,3-dioxolane) (L) | 5.93(s) |
| $T^{BOM}$ | $CH_2$-(2,2-dimethyl-1,3-dioxolane-CH$_2$OBn) | 5.94(d, J=2Hz) |
| $T^{BOM}$ | $CH_2$-(2,2-dimethyl-1,3-dioxolane) (D) | 5.91(s) |
| 6-OBn, 2-NH$^2$-purine | $CH_2CH_2OCH_3$ | 6.09(d, J=5Hz) |
| 6-Cl, 2 Cl-purine | $CH_2CH_2OH$ | 5.77(d, J=7Hz) |
| 6-Cl, 2 Cl-purine | $CH_2COOCH_3$ | 6.32(d, J=4Hz) |
| $T^{BOM}$ | $CH_2CH(OH)CH_2OCH_2CH_2C_6F_{13}$ | 5.94(d, J=2Hz) |
| $T^{BOM}$ | $CH_2CH(OCH_3)CH_2OCH_3$ | 5.93(d, J=2Hz) |
| $T^{BOM}$ | $CH_2CH(OH)CH_2OCH_2CH$—$CH$—$CH_2OBn$ (with 2,2-dimethyl-1,3-dioxolane ring on CH—CH) | 5.92(d, J=1.5Hz) |
| $T^{BOM}$ | $CH_2CH(OCH_3)CH_2OCH_2CH$—$CH$—$CH_2OBn$ (with 2,2-dimethyl-1,3-dioxolane ring on CH—CH) | 5.90(d, J=1.5Hz) |
| 4-NH$_2$-1-methyl-pyrazolo[3,4-d]pyrimidine | $CH_2COOCH_3$ | 6.63(d, 5Hz) |

TABLE 1-continued
Examples of further 2'-OH modifications
(b)
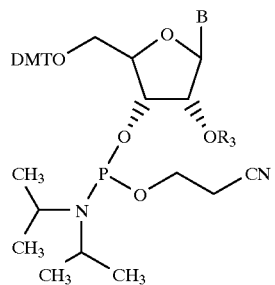
| B | R₃ | δ in $^{31}$P—NMR (ppm) |
|---|---|---|
| 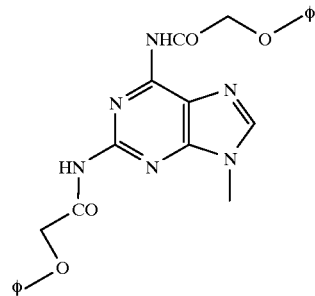 | CH₂CH₂OCH₃ | 150.18; 150.01 |
| 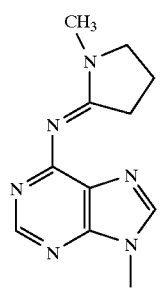 | CH₂CH₂OCH₃ | 149.87; 150.42 |
| 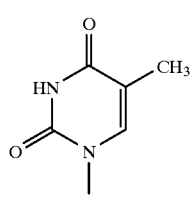 | CH₂CH₂OCH₃ | 150.14; 150.02 |
| 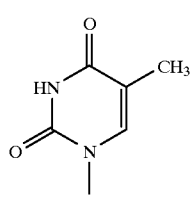 | (CH₂CH₂O)₃CH₃ | 149.95; 149.88 |

TABLE 1-continued

Examples of further 2'-OH modifications

| Base | R (2'-O substituent) | Mass |
|---|---|---|
| 1-methylthymine | $(CH_2CH_2O)_3C_{10}H_{21}$ | 150.12; 150.06 |
| 1-methylthymine | $CH_2CH(OMe)CH_2OC_{16}H_{33}$ | 150.10; 150.01 |
| 1-methylthymine | 2,2-dimethyl-1,3-dioxolan-4-ylmethyl (D) | 150.09; 150.02 |
| 1-methylthymine | 2,2-dimethyl-1,3-dioxolan-4-ylmethyl (L) | 150.08; 149.91 |
| 4-(1,2,4-triazol-1-yl)-1-methyl-5-methylpyrimidin-2-one | $CH_2CH_2OCH_3$ | 150.25; 149.43 |
| 4-(1,2,4-triazol-1-yl)-1-methyl-5-methylpyrimidin-2-one | $(CH_2CH_2O)_3CH_3$ | 150.34; 149.47 |

TABLE 1-continued

Examples of further 2'-OH modifications

| Base | 2'-OH modification | Values |
|---|---|---|
| 4-(1,2,4-triazol-1-yl)-5-methyl-1-methyl-pyrimidin-2-one | $(CH_2CH_2O)_3C_{10}H_{21}$ | 150.48; 149.60 |
| 4-(1,2,4-triazol-1-yl)-5-methyl-1-methyl-pyrimidin-2-one | $CH_2CH(OMe)CH_2OC_{16}H_{33}$ | 150.73; 149.33 |
| 4-(1,2,4-triazol-1-yl)-5-methyl-1-methyl-pyrimidin-2-one | 2,2-dimethyl-1,3-dioxolan-4-yl-CH$_2$ (D) | 150.80; 149.61 |
| 4-NHCOφ-5-methyl-1-methyl-pyrimidin-2-one | $CH_2CH_2OCH_3$ | 150.17; 150.09 |
| 5-(1-propynyl)-1-methyl-uracil | $CH_2CH_2OCH_3$ | 150.19; 149.76 |
| 4-(N-methylpyrrolidin-2-ylidene)amino-5-(1-propynyl)-1-methyl-pyrimidin-2-one | $CH_2CH_2OCH_3$ | 149.51; 149.23 |

TABLE 1-continued

Examples of further 2'-OH modifications

| Base | R | Data |
|---|---|---|
| Uracil, N1-substituted | $CH_2CH_2OCH_3$ | 150.60; 150.18 |
| 4-(1,2,4-triazol-1-yl)-pyrimidin-2-one, N1-substituted | $CH_2CH_2OCH_3$ | 151.18; 149.49 |
| Thymine, N1-substituted | $CH_2CH(CH_3)OCH_3$ | 150.82; 150.74 |
| Thymine, N1-substituted | $CH_2CH(OCH_3)CH_2OCH_3$ | 150.92; 150.76 |
| 2,6-bis(1-methylpyrrolidin-2-ylidenamino)-purine, N9-substituted | $CH_2CH_2OCH_3$ | 150.71; 150.96 |

EXAMPLE A17

5.0 g of the product prepared in Example A6 are dissolved in 50 ml of THF. After the addition of 0.21 g of NaH, the reaction mixture is heated at 60° C. for 45 minutes, and then 1.57 g of diethylene glycol chloroethyl methyl ether are added thereto. Finally, stirring is continued for a total of 54 hours at 60° C. After the 8th and 42nd hours a further 0.05 g of NaH and 0.4 g of diethylene glycol chloroethyl methyl ether are added. The mixture is cooled and then poured onto water and extracted with ethyl acetate. Drying over $MgSO_4$ and concentration of the extract by evaporation yield the compound (A17), which is then chromatographed on silica gel with hexane/ethyl acetate (1:1).

(A17)

¹H-NMR (250 MHz, CDCl₃): 1.60 (s, C$\underline{H}_3$); 3.33 (s, OC$\underline{H}_3$); 5.47 (AB, C$\underline{H}_2$); 5.93 [d, $\underline{H}$—C(1')]; 7.65 [s, $\underline{H}$—C(6)]. MS: 840 (M⁻).

EXAMPLE A18

3.2 g of the product prepared in Example A17 are hydrogenated in 35 ml of tetrahydrofuran over 0.6 g of Pd/C (5%) under normal pressure and at 22° C. After 1 hour (H₂-uptake 96%), the hydrogenation mixture is filtered until clear and then concentrated by evaporation. The residue is dissolved in 30 ml of methanol and 3.5 ml of a 30% solution of NaOCH₃ in methanol are added thereto. After stirring for 24 hours at 20° C., the reaction solution is poured onto water and extracted with ethyl acetate. Drying over MgSO₄ and concentration of the extract by evaporation yield the compound (A18).

(A18)

1H-NMR (250 MHz, CDCl₃): 1.60 (s, C$\underline{H}_3$); 3.55 (s, OC$\underline{H}_3$); 5.96 [d, J=2 Hz, $\underline{H}$—C(1')]; 7.62 [s, $\underline{H}$—C(6)]; 8.96 (s, N$\underline{H}$). MS: 720/722/724 (M⁺).

EXAMPLE A19

2.3 g of the product prepared in Example A18 are dissolved in 75 ml of methanol and hydrogenated at 35° C. by the addition of 1.15 g of sodium acetate and 1.0 g of Pd/C (5%). After 43 hours, the catalyst is filtered off and the filtrate is concentrated. To remove salts, the residue is filtered over silica gel with ethyl acetate/methanol (4:1). The compound (A19) is obtained.

(A19)

1H-NMR [250 MHz, methanol (D₄)]: 1.72 (s, C$\underline{H}_3$); 3.22 (s, OC$\underline{H}_3$); 5.80 [d, J=5 Hz, $\underline{H}$—C(1')]; 7.78 [s, $\underline{H}$—C(6)]. MS: 404 (M).

EXAMPLE A20

400 mg of the product prepared in Example A19 are dissolved in 8 ml of absolute pyridine. At 20° C., 0.34 g of DMTCl is added and the reaction mixture is stirred for 20 hours, then diluted with 30 ml of methylene chloride and poured onto water. The organic phase is washed with water a second time, then dried (MgSO₄) and concentrated by evaporation. The residue is chromatographed on silica gel with ethyl acetate/triethylamine (97:3) to yield the compound (A20).

(A20)

¹H-NMR (250 MHz, CDCl₃; all signals are broad): 1.40 (s, CH₃); 3.35 (s, OCH₃); 3.70 (s, 2×OCH₃); 6.02 (s, H—C(1'); 7.66 [s, H—C(6)]. MS: 705 (M–H).

EXAMPLE A21

0.39 g of the product prepared in Example A20 in 2.5 ml of methylene chloride is added dropwise to 0.12 g of diisopropylammonium tetrazolide and 0.20 g of cyanoethyltetraisopropylphosphorus amidite in 2.5 ml of absolute methylene chloride. After stirring for 28 hours at 20° C., the reaction solution is poured onto a saturated aqueous NaHCO₃ solution and extracted with methylene chloride. The residue is concentrated by evaporation and then chromatographed on silica gel with ethyl acetate/triethylamine (97:3) to yield the compound (A21).

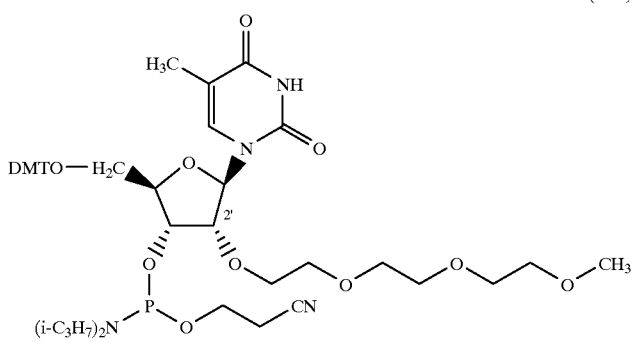

(A21)

¹H-NMR (250 MHz, CDCl₃): The protons of H—C(1') appear as doublets at 6.02 and 6.07 ppm. ³¹P-NMR (CDCl₃): 149.95 and 149.88 ppm

EXAMPLE A22

21.4 g of uracil are suspended in 250 ml of dichloroethane. 116 g of BSA are added thereto and the reaction mixture is then heated to 80°. After 30 minutes, a solution forms. The solution is cooled to 40° C. and 50.0 g of the product prepared in Example A3, dissolved in 350 ml of dichloroethane, and 27.4 g of SnCl₄ are added thereto. The solution is then kept at 80° C. for 5 hours, cooled and then poured onto saturated NaHCO₃ solution. The resulting 2-phase suspension is filtered and the organic phase is separated off. The aqueous phase is extracted again with CH₂Cl₂. The collected extracts are dried over MgSO₄ and concentrated by evaporation. The residue is digested in acetonitrile to yield the compound (A22).

(A22)

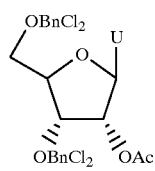

NMR (250 MHz, CDCl₃): 2.22 (s, OAc), 5.35 (t, H—C (2')), 6.07 (d, J=4 Hz, H—C(1')), 5.53 and 7.23 (each d, J=8 Hz, H—C(5) and H—C(6)), 8.57 (s, NH). MS: 602

EXAMPLE A23

At 60° C., 35.6 g of the product prepared in Example A4, dissolved in 300 ml of THF, are added to 60 ml of THF and 1.47 g of NaH (100%) and heating is continued for 1 hour. 14.0 g of R-(–)glycidyl tosylate are introduced in portions. After 2.5 hours, a further 0.1 g of NaH is added. The reaction mixture is heated for 4 hours and then cooled, poured onto ice and extracted with ethyl acetate. The extract is concentrated by evaporation and then chromatographed (silica gel, toluene/ethyl acetate 9:1) to yield the compound (A23).

(A23)

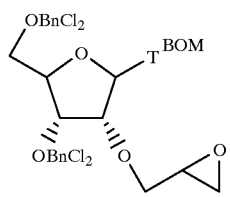

NMR (250 MHz, CDCl₃): 1.59 (s, CH₃), 5.48 (AB, CH₂), 5.92 (s, 1.5 Hz, H—C(1')), 7.62 (s, H—C(6)). FAB-MS: 751 (M+H)

EXAMPLE A24

5.1 g of the product prepared in Example A23 and 4.93 g of 1-hexadecanol are dissolved in 50 ml of CH₂Cl₂. 0.96 g of boron trifluoride diethyl etherate (d=1.13 g/ml) is added thereto. The solution is stirred at room temperature for 19 hours, then poured onto H₂O and extracted with CH₂Cl₂. The extract is concentrated by evaporation and then chromatographed over silica gel (ethyl acetate/hexane 1:1) to yield the compound (A24).

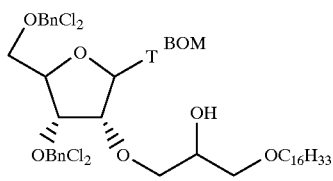

(A24)

NMR (250 MHz, CDCl$_3$): 1.60 (s, CH$_3$), 5.47 (AB, CH$_2$), 5.93 (d, J=1.5 Hz, H—C(1')), 7.63 (s, H—C(6)). FAB-MS: 1027 (M+Cl)$^-$

EXAMPLE A25

3.45 g of the product prepared in Example A24 are heated at 60° C. for 45 minutes in 35 ml of THF with 0.15 g of NaH (100%). 0.63 g of MeI are then added thereto and the reaction mixture is heated for a further 1.5 hours. The reaction mixture is then cooled, poured onto water and extracted with ethyl acetate. The residue is concentrated by evaporation and then filtered in toluene over a short column of silica gel to yield the compound (A25).

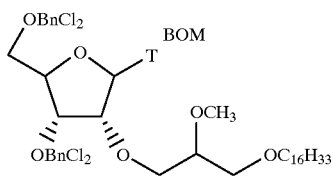

(A25)

NMR (250 MHz, CDCl$_3$): 1.59 (s, CH$_3$), 5.45 (AB, CH$_2$), 5.93 (d, J=1.5 Hz, H—C(1')), 7.63 (s, H—C(6)). MS (DCl): 1024 (M+NH$_4$)$^+$

EXAMPLE A26

3.3 g of the product prepared in Example A25 are hydrogenated in 70 ml of THF over 0.7 g of Pd/C (33 hours, H$_2$-uptake 104%). The reaction mixture is filtered and concentrated by evaporation. The residue is dissolved in 10 ml of THF and 10 ml of methanol, and NaOCH$_3$/HOCH$_3$ solution (30%) is added thereto. The reaction mixture is stirred at room temperature for 24 hours and then concentrated to approximately half its volume, poured onto water and extracted with ethyl acetate. The extract is concentrated by evaporation and then chromatographed over silica gel (ethyl acetate/toluene 1:2) to yield the compound (A26).

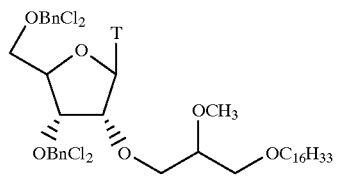

(A26)

NMR (250 MHz, CDCl$_3$): 1.62 (s, CH$_3$), 3.40 (s, OCH$_3$), 5.98 (d, J=2 Hz, H—C(1')), 7.62 (s, H—C(6)), 8.57 (s, NH). MS (DCl): 886

EXAMPLE A27

1.21 g of the product prepared in Example A26 are hydrogenated with 50 ml of methanol and 5 ml of toluene over 0.2 g of Pd/C (10%) and 0.258 g of MgO (2 hours, H$_2$-uptake 220 ml). The reaction mixture is filtered, concentrated by evaporation and filtered over silica gel (removal of Mg salts) to yield the compound (A27).

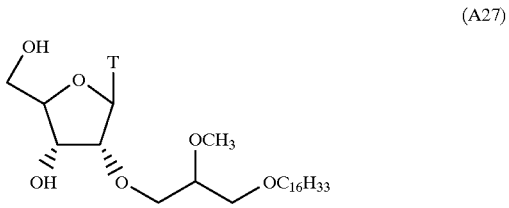

(A27)

NMR (250 MHz, DMSO-D$_6$): 1.72 (s, CH$_3$), 5.05 (d, OH), 5.18 (t, OH), 5.84 (d, J=6 Hz, H—C(1')), 7.77 (s, H—C(6)). FAB-MS: 569 (M-H).

EXAMPLE A28

0.83 g of the product prepared in Example A28 is dissolved in 50 ml of pyridine and the solution is concentrated by evaporation. 8 ml of pyridine and 0.6 g of DMT chloride are added to the residue and the reaction mixture is then stirred at room temperature for 44 hours. The solution is poured onto H$_2$O and extracted with ethyl acetate. The residue is concentrated by evaporation and then chromatographed over silica gel (toluene/ethyl acetate 1:1+1% NEt$_3$ addition) to yield the compound (A28).

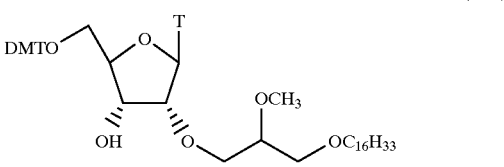

(A28)

NMR (250 MHz, CDCl$_3$): 1.35 (s, CH$_3$), 3.47 (s, OCH$_3$), 3.80 (s, OCH$_3$), 6.03 (d, J=4 Hz, H—C(1')), 7.64 (s, H—C(6)), 8.20 (s, NH). FAB-MS: 873 (M+H).

EXAMPLE A29

10 ml of CH$_2$Cl$_2$, 0.245 g of diisopropylammonium tetrazolide and 0.39 g of cyanoethyltetraisopropylphosphorus diamidite are added to 0.95 g of the product prepared in Example A28. After stirring for 3 days at room temperature, the reaction mixture is poured onto saturated NaHCO$_3$ solution and extracted with CH$_2$Cl$_2$. The residue is concentrated by evaporation and then chromatographed over silica gel (toluene/ethyl acetate 2:1+1% NEt$_3$ addition) to yield the compound (A29).

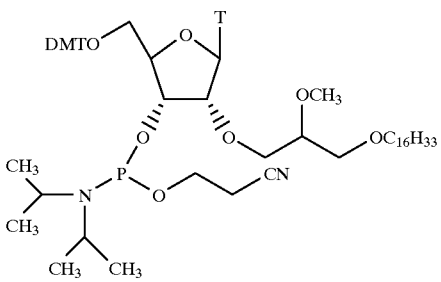

(A29)

$^1$H-NMR (250 MHz, CDCl$_3$): 5.97 and 6.05 (each d, J=4 Hz, each H—C(1)), 7.62 and 7.70 (each s, each H—C(6)). P-NMR (250 MHz, CDCl$_3$): 150.012 and 150.102. FAB-MS: 1071 (M–H).

EXAMPLE A30

15.6 g of hypoxanthine and 46.6 g of BSA are heated under reflux in 300 ml of dichlorethane. After 30 minutes a solution forms. 30.0 g of the product prepared in Example A3 and 16.5 g of TMS triflate are added to the solution and boiling is continued for a further 16 hours. The reaction mixture is cooled and then poured onto saturated NaHCO$_3$ solution and the resulting suspension is filtered. The filtrate is extracted with CH$_2$Cl$_2$. The organic phase is dried over MgSO$_4$ and concentrated by evaporation. The residue is chromatographed (methanol/ethyl acetate 1:1) to yield the compound (A30).

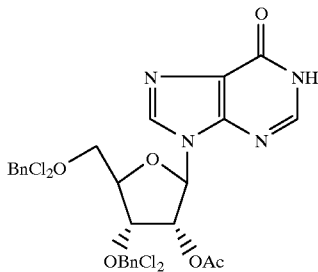

(A30)

$^1$H-NMR (250 MHz, CDCl$_3$): 6.22 (d, 3 Hz, H—C(1')), 8.14 and 8.37 (each s, H—C(2) and H—C(8)). FAB-MS: 625 M–H

EXAMPLE A31

3.8 g of the product prepared in Example A30 are introduced in 150 ml of CH$_2$Cl$_2$. While boiling, a mixture of 4.8 ml of SOCl$_2$ and 2.4 ml of DMF are added drop-wise thereto. The reaction mixture is boiled for a further 3 hours and then a further 1.2 ml of SOCl$_2$ and 0.6 ml of DMF are added thereto. The reaction mixture is boiled for a total of 5.5 hours and then introduced into a saturated NaHCO$_3$ solution, stirred for 20 minutes and extracted with CH$_2$Cl$_2$. The extract is dried over MgSO$_4$ and concentrated by evaporation to yield the compound (A31).

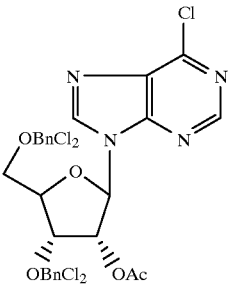

(A31)

NMR (250 MHz, CDCl$_3$): 5.83 (dd, H—C(2')), 6.33 (d, J=3 Hz, H—C(1')), 8.47 and 8.73 (each s, H—C(2) and H—C(8)). MS: 664

EXAMPLE A32

30.4 g of the product prepared in Example A31 are dissolved in 200 ml of methanol and 100 ml of THF and 16.9 g of 30% NaOMe/methanol are added dropwise thereto. The reaction mixture is stirred for 3 hours and then poured onto H$_2$O and extracted with ethyl acetate. The extract is dried over MgSO$_4$ and concentrated by evaporation to yield the compound (A32).

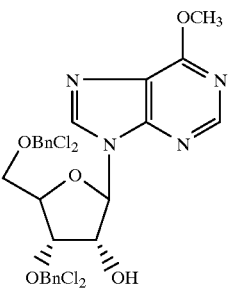

(A32)

NMR (250 MHz, CDCl$_3$): 4.20 (s, OCH$_3$), 6.10 (d, J=6 Hz, H—C(1')), 8.17 and 8.48 (each s, H—C(2) and H—C(8)). MS: 598

EXAMPLE A33

1.17 g of NaH (100%) are added to 25.4 g of the product prepared in Example A32 in 250 ml of THF. While boiling, 6.76 g of 2-bromoethyl methyl ether are added dropwise thereto. The reaction mixture is boiled for a further 6 hours and then a further 0.5 g of NaH and 1.9 ml of bromide are added thereto. After 23 hours the reaction mixture is cooled and poured onto H$_2$O, extracted with ethyl acetate and concentrated by evaporation. The residue is chromatographed (silica gel, hexane/acetone 2:1) to yield the compound (A33).

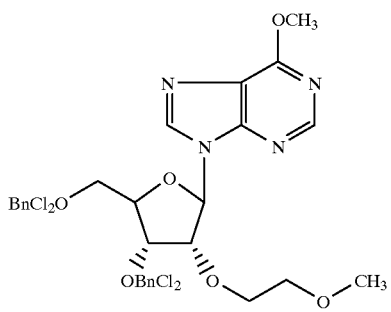

(A33)

¹H-NMR (250 MHz, CDCl₃): 3.27 (OCH₃), 4.20 (OCH₃), 6.27 (d, J=5 Hz, H—C(1')), 8.24 and 8.52 (each s, H—C(2) and H—C(8)). MS(DCI): 656

EXAMPLE A34

2.2 g of the product prepared in Example A33 is hydrogenated in 45 ml of methanol with 0.66 g of Pd/C (10%) and with the addition of 402 ml of MgO. After 13 hours (H₂-uptake 485.5 ml of H₂), the mixture is filtered until clear and concentrated by evaporation. To remove magnesium salts, the residue is chromatographed over silica gel (ethyl acetate/methanol 9:1) to yield the compound (A34).

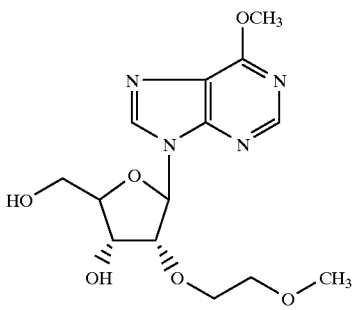

(A34)

NMR (250 MHz, DMSO(-d₆)): 4.4 (t, OH), 5.23 (OH), 5.94 (d, J=6.5 Hz, H—C(1')), 8.40 and 8.55 (each s, H—C(2) and H—C(8)). FAB MS: 339 (M-H)⁻.

EXAMPLE A35

2.46 g of the product prepared in Example A34 are dissolved in 80 ml of methanol and introduced into an autoclave. 20 g of NH₃ are forced in and the apparatus is kept at 120° C. for 12 hours (internal pressure: 17 bar). The reaction mixture is concentrated by evaporation and chromatographed on silica gel (ethyl acetate/methanol) to yield the compound (A35).

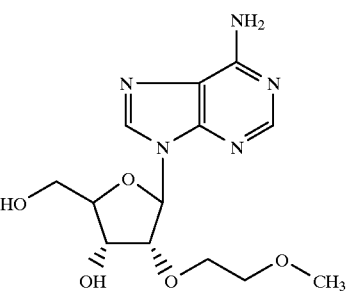

(A35)

NMR (250 MHz, DMSO-D₆): 5.32 (d, OH), 5.60 (t, OH), 6.15 (d, J=6 Hz, H—C(1')), 8.33 and 8.57 (each s, H—C(2) and H—C(8)). MS (DCI): 326 (M+H).

EXAMPLE A36

0.48 g of the product obtained in Example A35 is dissolved in 5 ml of methanol and 0.28 g of N-methyl-2,2-dimethoxypyrrolidine is added thereto. The reaction mixture is stirred for 18 hours and then concentrated by evaporation. Pyridine is added twice to the residue, which is then concentrated by evaporation. The residue that remains is dissolved in 10 ml of pyridine and stirred at room temperature with 0.5 g of DMT chloride for 40 hours. The resulting mixture is poured onto H₂O and extracted with CH₂Cl₂. The extract is concentrated by evaporation and then chromatographed over silica gel (ethyl acetate/methanol 9:1) to yield the compound (A36).

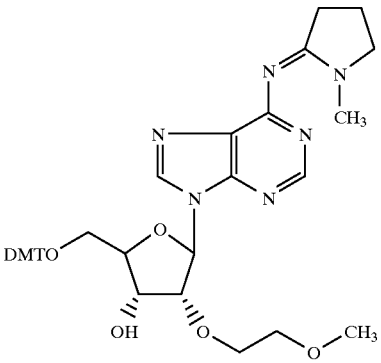

(A36)

NMR (250 MHz, CDCl₃): 3.09 (s, NMe), 3.72 (s, OCH₃), 6.08 (d, J=6 Hz, H—C(1')), 7.98 and 8.43 (each s, H—C(2) and H—C(8)). FAB MS: 709 (M+H)

EXAMPLE A37

0.63 g of the trityl derivative obtained in Example A36 in 6 ml of CH₂Cl₂ are added to 0.38 g of cyanoethyltetraisopropylphosphorus diamidite and 0.24 g of diisopropylammonium tetrazolide in 6 ml of CH₂Cl₂. The reaction mixture is stirred for 40 hours and then poured onto saturated NaHCl₃ solution and extracted with CH₂Cl₂. The extract is concentrated by evaporation and then chromatographed (ethyl acetate+1% NEt₃) to yield the compound (A37).

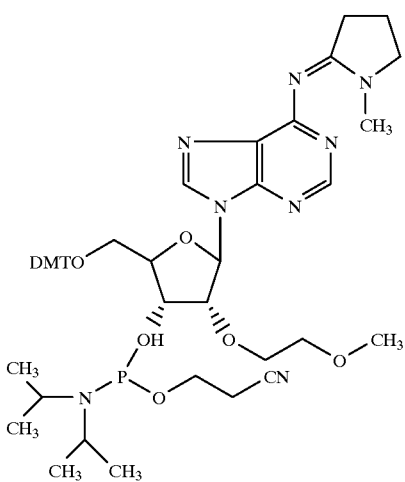

(A37)

$^{31}$P-NMR (250 MHz, CDCl$_3$): 149.8 and 150.4. FAB-MS: 909 (M+H)

EXAMPLE A38

7.1 g of the epoxide prepared in Example A23 are dissolved in 70 ml of THF, 0.43 g of NaBH$_4$ is added thereto and the reaction mixture is stirred at room temperature. 0.5 g of BF$_3$.OEt$_2$ are added thereto. After a total of 26 hours, the reaction mixture is poured onto water and extracted with ethyl acetate. Concentration by evaporation yields the compound (A38).

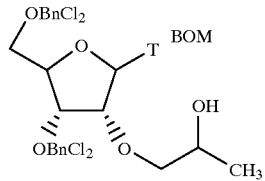

(A38)

NMR (250 MHz, CDCl$_3$): 1.16 (d, J=7.5 Hz, CH$_3$), 1.61 (s, CH$_3$), 5.48 (AB, CH$_2$), 5.92 (d, J=1 Hz, H—C(1')), 7.69 (s, H—C(6)). FAB-MS: 787 (M+Cl)$^-$.

EXAMPLE A39

6.9 g of the alcohol obtained in Example A38 are methylated with 1.56 g of NaH (100%) and 1.56 g of MeI in 70 ml of THF (60° C., 5 hours). The customary working-up yields the compound (A39).

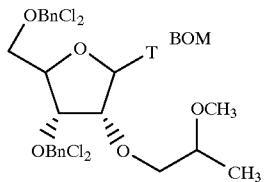

(A39)

NMR (250 MHz, CDCl$_3$): 1.13 (d, J=7.5 Hz, CH$_3$), 1.60 (s, CH$_3$), 3.33 (s, OCH$_3$), 5.49 (AB, CH$_2$), 5.95 (A, J=2 Hz, H—C(1')), 7.64 (s, H—C(6)). MS (DCI): 766 (M$^-$).

EXAMPLE A40

14.4 g of the derivative prepared in accordance with Example A4 are heated at 60° C. for 30 minutes in 150 ml of THF and 0.65 g of NaH (100%). The reaction mixture is then cooled to 25° C. and 5.92 g of D-α,β-isopropylidene glycerol-γ-tosylate are added thereto. After 1.5 hours, the reaction mixture is stirred at 60° C. for a further 3 hours. The reaction mixture is cooled and poured onto water, extracted with ethyl acetate and concentrated by evaporation. The residue is chromatographed over silica gel (toluene/ethyl acetate 4:1) to yield the compound (A40).

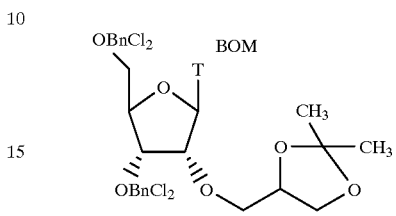

(A40)

NMR (250 MHz, CDCl$_3$): 1.34 and 1.41 (each s, each CH$_3$), 1.58 (s, CH$_3$), 5.48 (AB, CH$_2$), 5.92 (d, J=1.5 Hz, H—C(1')), 7.68 (s, H—C(6)). MS (DCI): 843 (M+Cl)$^-$.

EXAMPLE A41

3.13 g of the phosphorus amidite prepared in accordance with Example A13 are dissolved in 50 ml of acetonitrile. 9.4 ml of NEt$_3$ and 6.17 g of 1,2,4-triazole are added thereto. With stirring, 1.53 g of POCl$_3$ are then added dropwise thereto in such a manner that the temperature does not exceed 30° C. The reaction mixture is stirred for a further 4 hours at room temperature and then poured onto 1 N NaHCO$_3$ (150 ml) and extracted with ethyl acetate. The extract is concentrated by evaporation, dissolved in a small amount of CH$_2$Cl$_2$ and stirred into 100 ml of n-pentane. The compound (A41) precipitates.

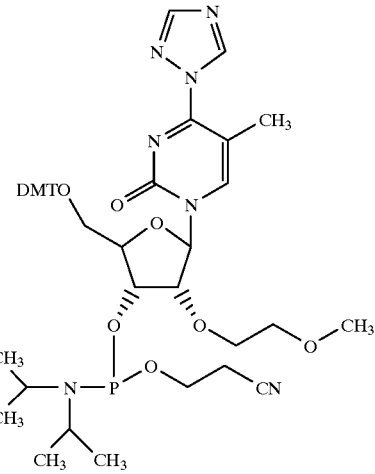

(A41)

$^1$H-NMR (250 MHz, CDCl$_3$): 6.02 and 6.06 (each d, J=1.5 Hz, H—C(1')), 8.44 and 8.47 (each s, H—C(6)), 8.07 and 9.35 (each s, triazole H). $^{31}$P-NMR (250 MHz, CDCl$_3$): 149.433 and 150.253 MS (DCI): 869 (M$^-$)

EXAMPLE A42

8.88 g of N$^2$-isobutyryl-O$^6$-benzylguanine [prepared in accordance with analogous instructions in Jenny, T. F., Schneider, K. C., Benner, S. A., Nucleosides and Nucleotides 11:1257–1261 (1992)] and 34.8 g of N,O-bis(trimethylsilyl)acetamide are suspended in 130 ml of toluene and heated at 100° C. until a solution forms. At 50° C., 13.0 g of the ribose derivative prepared in accordance with Example A3 and 6.33 g of trifluoromethanesulfonic acid trimethylsilyl ester are added thereto. The colourless solution is stirred for 4 hours at 100° C., cooled and then poured onto 200 ml of saturated NaHCO₃ solution. The reaction mixture is then extracted with ethyl acetate, dried over MgSO₄ and concentrated by evaporation. The residue is chromatographed over 1.2 kg of silica gel (toluene/ethyl acetate 4:1) to yield the compound (A42).

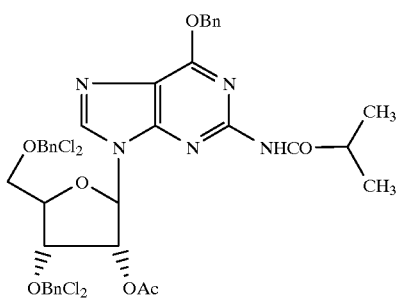
(A42)

¹H-NMR (250 MHz, CDCl₃): 1.26 (d, J=7.5 Hz, CH₃), 2.23 (s, OAc), 5.61 (AB, OCH₂), 5.78 (dd, H—C(2')), 6.19 (d, J=3 Hz, H—C(1')), 7.83 (s, NH), 8.00 (s, H—C(8)). MS (DCI): 801 (M⁻).

EXAMPLE A43

0.83 g of a 30% NaOMe/methanol solution is added to 7.4 g of the derivative prepared in Example A42 dissolved in 80 ml of methanol, and the reaction solution is stirred at room temperature for 30 minutes. The solution is poured onto H₂O and extracted with ethyl acetate. The extract is dried over MgSO₄ and then concentrated by evaporation to yield the compound (A43).

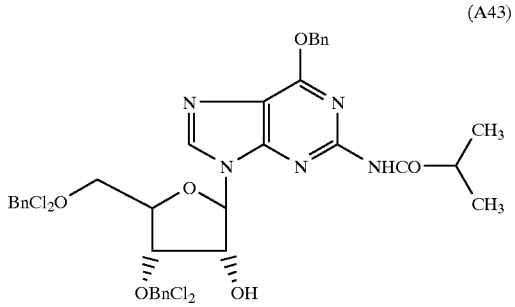
(A43)

NMR (250 MHz, CDCl₃): 1.29 (d, J=7.5 Hz, CH₃), 5.61 (AB, OCH₂), 5.99 (d, J=6 Hz, H—C(1')), 7.97 (s, NH), 8.04 (s, H—C(8)). MS (DCI): 760 (M+H)⁺

EXAMPLE A44

630 mg of NaH (100%) are added to 9.0 g of the compound prepared in accordance with Example A43 in 100 ml of THF and the reaction mixture is stirred for 15 minutes. 1.97 g of 2-bromoethyl methyl ether are then sprayed into the reaction mixture. After 25 hours, a further 2.0 g of bromide are added. The reaction mixture is stirred for a total of 48 hours, then poured onto water and extracted with ethyl acetate. The extract is concentrated by evaporation and chromatographed over silica gel (toluene/ethyl acetate 4:1) to yield the compound (A44).

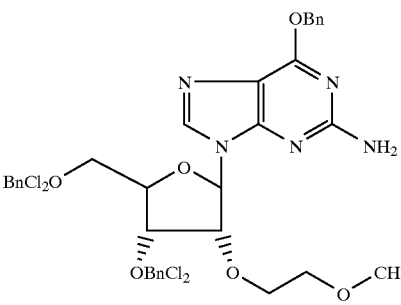
(A44)

NMR (250 MHz, CDCl₃): 3.28 (s, OCH₃), 5.56 (AB, OCH₂), 6.10 (d, J=5 Hz, H—C(1')), 7.90 (s, H—C(8)). FAB-MS: 748 (M+H)⁺.

EXAMPLE A45

Starting from compound (A3), further bases are introduced. The products are listed in Table 2.

TABLE 2

Examples of the introduction of further bases

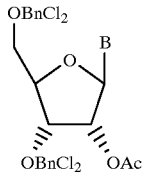

| B | δ H—C(1') in ¹H—NMR (in ppm) |
|---|---|
| 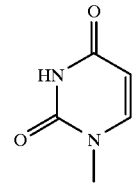 | 6.07(d, J=4Hz) |
| 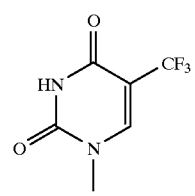 | 6.19(d, J=4Hz) |
| 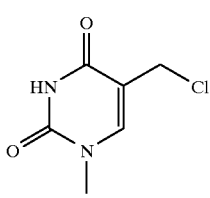 | 6.08(d, J=5Hz) |

TABLE 2-continued

Examples of the introduction of further bases

[Structure: sugar with OBnCl₂ (5'), OBnCl₂ (3'), OAc (2'), B (1')]

| B | δ H—C(1') in ¹H—NMR (in ppm) |
|---|---|
| thymine, N1-methyl (5-CH₃, HN, C=O, C=O) | 6.10(d, J=4.5Hz) |
| N3-(φ-CH₂-O-CH₂), N1-methyl thymine | 6.05(d, J=4.5Hz) |
| N3-(φ-CH₂-O-CH₂), N1-methyl uracil | 6.02(d, J=3Hz) |
| 5-(CH₂-O-CH₂CH₂-O-CH₃) uracil, N1-methyl | 5.95(d, J=4Hz) |
| 5-(CH₂OH) uracil, N1-methyl | 6.12(d, J=5Hz) |
| 2,6-dichloropurine, N9-methyl | 6.27(d, J=6Hz) |

TABLE 2-continued

Examples of the introduction of further bases

[Structure: sugar with OBnCl₂ (5'), OBnCl₂ (3'), OAc (2'), B (1')]

| B | δ H—C(1') in ¹H—NMR (in ppm) |
|---|---|
| 6-NH₂, 2-Cl, N9-methyl purine | 6.18(d, J=4Hz) |
| 6-OBn, 2-NHCO-iPr, N9-methyl purine | 6.19(d, J=3Hz) |
| 6-OCONφ₂, 2-NHCOCH₃, N9-methyl purine | 6.14(d, J=4Hz) |
| hypoxanthine, N9-methyl | 6.22(d, J=3Hz) |
| 6-Cl, N9-methyl purine | 6.32(d, J=4Hz) |
| 2-NHCO-iPr, hypoxanthine, N9-methyl | 6.06(d, J=5Hz) |

TABLE 2-continued

Examples of the introduction of further bases

[Structure: sugar with OBnCl₂ at 5'-CH₂, OBnCl₂ at 3', OAc at 2', B at 1']

| B | δ H—C(1') in ¹H—NMR (in ppm) |
|---|---|
| [6-benzamidopurine structure, NHCOφ on purine] | 6.33(d, J=4Hz) |
| [4-amino-5-bromo-7-methyl-7-deazapurine; NH, CN, Br substituents] | 6.12(d, J=4Hz) |

EXAMPLE B

Preparation of Oligonucleotides

Oligonucleotides are bound to a solid carrier (controlled pore glass, CPG) using the dimethoxytritylated and 3'-activated [3'-(β-cyanoethoxy-di(isopropylamino) phosphorus amidite)] nucleosides according to the invention or natural nucleosides similarly activated, and the synthesis is carried out on a DNA synthesiser (Applied Biosystems, Model 380 B, standard phosphorus amidite chemistry and iodoxidation) in accordance with the manufacturer's standard protocols [see also "Oligonucleotide synthesis, a practical approach" M. J. Gait; IRL Press 1984 (Oxford-Washington D.C.)]. After the coupling of the final nucleoside building block, the 5'-protected oligonucleotide is removed from the carrier, with simultaneous removal of all other protecting groups, by treatment overnight with concentrated aqueous ammonia and then purified by reverse-phase HPLC using 50 mM ammonium acetate buffer (pH 7)/acetonitrile. The 5'-dimethoxytrityl protecting group is then removed by treatment for 20 minutes with 80% aqueous acetic acid and the oligonucleotide is precipitated with ethanol and isolated by centrifugation. The purity of the oligonucleotide is tested by gel electrophoresis (polyacrylamide) and its identity by means of matrix-assisted laser desorption time-of-flight mass spectroscopy (MALDI-TOF MS).

EXAMPLE C1

Affinity; Interaction of the Oligonucleotides (anti-sense) with Complementary Oligoribonucleotide Sequences (sense)

The interaction of the oligonucleotides with the corresponding base-complementary oligomers of natural ribonucleotides is characterised by recording UV melt curves and the $T_m$ values determined therefrom. That standard method is described, for example, by Marky, L. A., Breslauer, K. J., Biopolymers 26:1601–1620 (1987).

A solution of the oligonucleotides and the corresponding base-complementary natural oligoribonucleotides in 10 mM phosphate buffer, 100 mM NaCl, 0.1 mM EDTA, pH=7.0 ($c=4\times10^{-6}$ M/oligonucleotide) is prepared and the change in the extinction at 260 nm is recorded as a function of the temperature (15 to 95° C.). The $T_m$ value is determined from the melt curves obtained (Table 3).

TABLE 3

Affinity
(a) SEQ ID NO: 1 TTTTtCTCTCTCTCT (vs. RNA)

[Structure: sugar with OH at 5'-CH₂, T base at 1', OH at 3', X at 2', H]

| X | Tm(° C.) | ΔTM(° C.) |
|---|---|---|
| H | 51.8 | 0 |
| O~~~OMe | 53.0 | +1.2 |
| O(~~O)₂Me | 52.7 | +0.9 |
| O(~~O)₃Me | 52.9 | +1.1 |
| O(~~O)₄Me | 52.2 | +0.4 |
| (D) O~CH(OH)~CH₂OH | 53.3 | +1.5 |
| (L) O~CH(OH)~CH₂OH | 53.3 | +1.5 |

(b) SEQ ID NO: 2 CTCGTACCtTTCCGTCC (vs. RNA)

[Structure: sugar with OH at 5'-CH₂, T base at 1', OH at 3', X at 2', H]

| X | Tm(° C.) | ΔTm(° C.) |
|---|---|---|
| H | 63.3 | 0 |
| O~~~OMe | 64.9 | +1.6 |

TABLE 3-continued

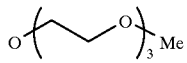

| | 64.0 | +0.7 |

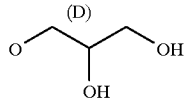

| | 64.1 | +0.8 |

(c) SEQ ID NO: 3 CTCGTACttttCCGGTCC (vs. RNA)

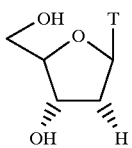

| X | Tm(° C.) | ΔTm(° C.)/mod. |
|---|---|---|
| H | 61.8 | 0 |
|  | 65.4 | +0.9 |
| 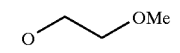 | 65.0 | +0.8 |
| 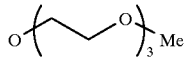 | 65.4 | +0.9 |

(d) SEQ ID NO: 4 tCCAGGtGtCCGCAtC (vs. RNA)

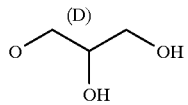

| X | Tm(° C.) | ΔTm(° C.)/mod. |
|---|---|---|
| H | 66.5 | 0 |
| 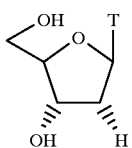 | 70.1 | +0.9 |
|  | 71.3 | +1.2 |
| 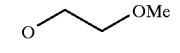 | 71.3 | +1.2 |

TABLE 3-continued (e) SEQ ID NO: 5 GCGttttttttttGCG (vs. RNA)

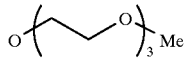

| X | Tm(° C.) | ΔTm(° C.)/mod. |
|---|---|---|
| H | 50.2 | 0 |
| 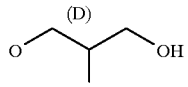 | 62.4 | +1.2 |
| 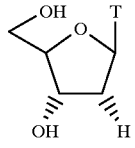 | 62.5 | +1.2 |
| 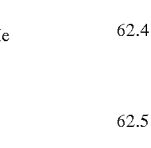 | 62.4 | +1.2 |

(f) SEQ ID NO: 6 tttttctctctctctC

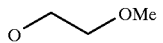

| B | X | Tm(° C.) | ΔTm(° C.)/mod. |
|---|---|---|---|
| T,C | H | 51.8 | 0 |
| T,5 Me—C |  | 75.8 | +1.6 |

Example D2: Specificity; interaction of the oligonucleotide with base-complementary oligoribonucleotides into which an incorrect nucleoside (Y) has been incorporated Solutions of the oligonucleotide with the corresponding base-complementary oligonucleotides having the sequences SEQ ID NO: 7 r(GGA CCG GAA YGG TAC GAG) in 10 mM phosphate buffer, 100 mM NaCl, 0.1 mM EDTA, pH 7, (c = 4 × 10$^{-6}$ M/oligonucleotide) are prepared and the change in the extinction at 260 nm is measured as a function of the temperature (15° C. to 95° C.). The $T_m$ value is determined from the curves. The results are given in Table 4.

EXAMPLE D2

Specificity; Interaction of the Oligonucleotide with Base-complementary Oligoribonucleotides into which an Incorrect Nucleoside (Y) has been Incorporated Solutions of the oligonucleotide with the corresponding base-complementary oligonucleotides having the sequences SEQ ID NO:7 r(GGA CCG GAA YGG TAC GAG) in 10 mM phosphate buffer, 100 mM NaCl, 0.1 mM EDTA, pH 7, (c=4×10$^{-6}$ M/oligonucleotide) are prepared and the change in the extinction at 260 nm is measured as a function of the temperature (15° C. to 95° C.). The $T_m$ value is determined from the curves. The results are given in Table 4.

TABLE 4

Specificity
sense: SEQ ID NO: 8 GAG CAU GGY AAG GCC AGG (RNA)
anti: SEQ ID NO: 9 CTC GTA CCt TTC CGG TCC (DNA)
Tm(° C.) and ΔTm

| | | | |
|---|---|---|---|
| Y = A | 63.3 | 65.0 | 64.1 |
| Y = C | 54.5 | 55.8 | 55.1 |
| | (−8.9) | (−9.2) | (−9.0) |
| Y = G | 61.6 | 61.4 | 59.5 |
| | (−1.7) | (−3.6) | (−4.5) |
| Y = U | 55.8 | 57.5 | 55.9 |
| | (−7.5) | (−7.5) | (−8.2) |
| Y = none | 59.4 | 57.8 | 56.4 |
| | (−3.9) | (−7.2) | (−7.7) |

EXAMPLE C3

Nuclease Stability; Enzymatic Hydrolysis of Different Oligonucleotides having the Sequence SEQ ID NO:10 d(TCC AGG TGT CCG ttt C)

14 μg of the synthetic oligonucleotide and 14 μg of the corresponding natural oligomer are incubated at 37° C. in 200 μl of 10% heat-inactivated serum from calf foetus (c=70 μg/ml). After 0.5, 1, 2, 4, 6, 24 and 48 hours, 15 μl of the reaction solution are quenched by the addition of 25 μl of 9 M urea and trisborate buffer (pH 7) and stored at −20° C. until being measured. The quenched reaction solutions are separated by means of polyacrylamide gel electrophoresis and the cleavage products are determined via the phosphorus content (phospho-imagers method). The ratio R of the sum of the concentrations of the fully intact oligonucleotide ($c_n^{(t)}$) and of the fragment formed by removal of the natural C building block from the 3' end ($c_{n-1}^{(t)}$) at a given time t to the starting concentration of the fully intact oligonucleotide at the time point t=0 ($c_n^{(0)}$) $R=(c_n^{(t)}+c_{n-1}^{(t)})/c_n^{(0)}$ is plotted on a graph against time. The half-times $\tau_{1/2}$ found—i.e. those times for which R=0.5—are

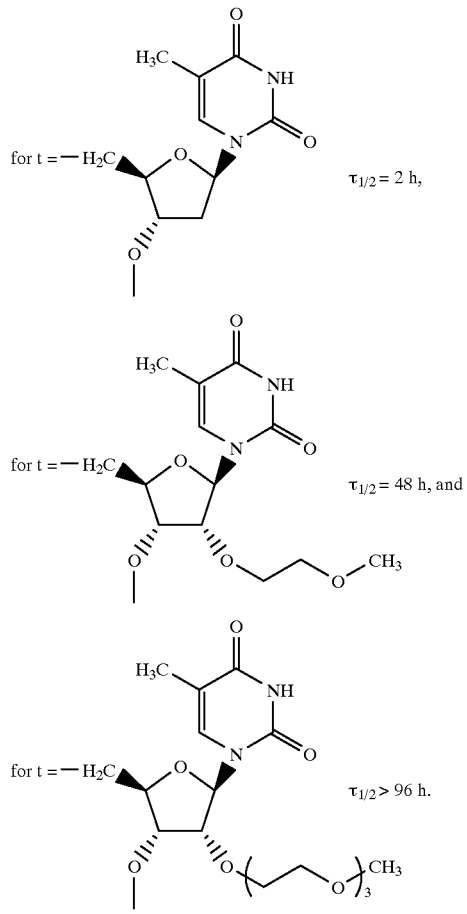

What is claimed is:

1. An oligonucleotide of formula V

 (V)

wherein x is a number from 1 to 200 and Y is a nucleotide bridge group; U, V and W are, each individually, identical or different radicals of natural or synthetic nucleosides, and at least one of the radicals U, V and/or W is a radical of formula VI

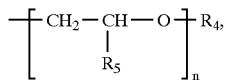 (VI)

wherein B is a purine or pyrimidine radical or an analogue thereof; and $R_3$ is a radical of formula Ia

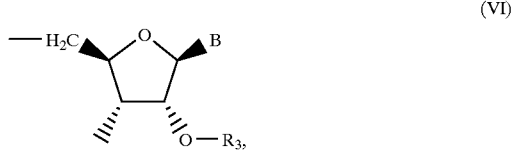 (Ia)

wherein $R_4$ is methyl;

$R_5$ is hydrogen; and n is the number 1;

said oligonucleotide being capable of base pairing with a complementary nucleic acid strand.

2. An oligonucleotide according to claim 1 wherein the bridge group Y is —P(O)O$^\ominus$—, —p(O)S$^\ominus$—, —P(S)S$^\ominus$—, —P(O)R$_{16}$—, —P(O)NR$_{17}$R$_{18}$— or —CH$_2$—, wherein R$_{16}$ is hydrogen or C$_1$–C$_6$alkyl, and R$_{17}$ and R$_{18}$, each independently of the other, have the definition of R$_{16}$.

3. An oligonucleotide according to claim 1 wherein the bridge group Y is —P(O)O$^\ominus$—.

4. An oligonucleotide according to claim 1 wherein x is a number from 1 to 100.

5. An oligonucleotide according to claim 4 wherein x is a number from 1 to 50.

6. An oligonucleotide according to claim 5 wherein x is a number from 3 to 29.

7. An oligonucleotide according to claim 1 wherein the radicals of formula VI are bonded terminally.

8. An oligonucleotide according to claim 1 wherein the radicals of formula VI are bonded between radicals of natural or synthetic nucleosides.

9. An oligonucleotide according to any of claims 7, or 8 wherein from 2 to 5 identical or different radicals of formula VI follow one another.

10. An oligonucleotide according to claim 1 comprising a total of from 4 to 30 nucleoside units and from 1 to 12 radicals of formula VI.

11. The use of an oligonucleotide of formula V according to claim 1 as a diagnostic agent in the detection of viral infections or genetic diseases.

12. An oligonucleotide of formula V according to claim 1 for use in a therapeutic method for the treatment of diseases in warm-blooded animals including humans by interaction with nucleotide sequences in the body.

13. A pharmaceutical composition comprising an effective amount of an oligonucleotide of formula V according to claim 1 alone or together with other active ingredients, a pharmaceutical carrier and, where appropriate, excipients.

14. An oligonucleotide according to claim 1, wherein the radicals of formula VI are bonded internally.

15. An oligonucleotide according to claim 1, wherein B is selected from the group consisting of uracil, thymine, 5-propynyluracil, cytosine, 5-methylcytosine, 5-propynylcytosine, hypoxanthine, adenine, 2-aminoadenine and guanine, the hydroxy and amino groups thereof being unsubstituted or substituted by a protecting group.

16. An oligonucleotide according to claim 1, wherein B is selected from the group consisting of uracil, thymine, 5-propynyluracil, cytosine, 5-methylcytosine, 5-propynylcytosine, hypoxanthine, adenine, 2-aminoadenine and guanine.

* * * * *

UNITED STATES PATENT AND TRADEMARK OFFICE
CERTIFICATE OF CORRECTION

PATENT NO. : 5,969,116
DATED : October 19, 1999
INVENTOR(S) : Pierre Martin

Page 1 of 1

It is certified that error appears in the above-identified patent and that said Letters Patent is hereby corrected as shown below:

Claim 1, in column 59, second line of the said claim should read:

--5' HO-U-(O-Y-O-V)x O-Y-O-W-OH 3' --.

Claim 2, in column 59, second line of the said claim should read:

--bridge group Y is —P(O)O$^\ominus$—, —P(O)S$^\ominus$—, —P(S)S$^\ominus$—. --.

Claim 9 in column 60, first line of the said claim should read:

--an oligonucleotide according to any of the claims 7, 14 or 8 --.

Signed and Sealed this

Second Day of October, 2001

Attest:

*Nicholas P. Godici*

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide
         comprising a modified sugar"

(xi) SEQUENCE DESCRIPTION: SEQ ID NO:1:

TTTTTCTCTC TCTCT                                        15

(2) INFORMATION FOR SEQ ID NO:2:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide
         comprising a modified sugar"

(xi) SEQUENCE DESCRIPTION: SEQ ID NO:2:

CTCGTACCTT TCCGTCC                                  17

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide
         comprising a modified sugar"

(xi) SEQUENCE DESCRIPTION: SEQ ID NO:3:

CTCGTACTTT TCCGGTCC                                 18

(2) INFORMATION FOR SEQ ID NO:4:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide
         comprising a modified sugar"

(xi) SEQUENCE DESCRIPTION: SEQ ID NO:4:

TCCAGGTGTC CGCATC                                   16

(2) INFORMATION FOR SEQ ID NO:5:

(i) SEQUENCE CHARACTERISTICS:
      (A) LENGTH: 16 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide
            comprising a modified sugar"

(xi) SEQUENCE DESCRIPTION: SEQ ID NO:5:

GCGTTTTTTT TTTGCG                                                      16

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide
            comprising a modified sugar"

(xi) SEQUENCE DESCRIPTION: SEQ ID NO:6:

TTTTTCTCTC TCTCTC                                                      16

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide
            comprising a modified sugar"

(xi) SEQUENCE DESCRIPTION: SEQ ID NO:7:

GGACCGGAAG GTACGAG                                                     17

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide
            comprising a modified sugar"

(xi) SEQUENCE DESCRIPTION: SEQ ID NO:8:

GAGCAGGAAG GCCAGG                                                      16

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide
            comprising a modified sugar"

(xi) SEQUENCE DESCRIPTION: SEQ ID NO:9:

CTCGTACCTT TCCGGTCC                                                    18

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide
            comprising a modified sugar"

(xi) SEQUENCE DESCRIPTION: SEQ ID NO:10:

TCCAGGTGTC CGTTTC                                        16